US008227635B2

(12) United States Patent
Bowden et al.

(10) Patent No.: US 8,227,635 B2
(45) Date of Patent: Jul. 24, 2012

(54) APPARATUS AND METHOD FOR CARRYING OUT MULTIPLE REACTIONS

(75) Inventors: Ned Bowden, Iowa City, IA (US); Michael Brett Runge, Iowa City, IA (US); Alan Lee Miller, III, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 163 days.

(21) Appl. No.: 12/476,978

(22) Filed: Jun. 2, 2009

(65) Prior Publication Data

US 2009/0299102 A1     Dec. 3, 2009

Related U.S. Application Data

(60) Provisional application No. 61/058,139, filed on Jun. 2, 2008, provisional application No. 61/059,221, filed on Jun. 5, 2008.

(51) Int. Cl.
*C07C 69/74* (2006.01)
(52) U.S. Cl. ........................................ 560/128; 560/127
(58) Field of Classification Search ........................ None
See application file for complete search history.

(56) References Cited

U.S. PATENT DOCUMENTS

| 5,683,356 A | * | 11/1997 | Halperin et al. | ............. | 604/5.01 |
| 6,018,060 A | * | 1/2000 | Baker et al. | .................... | 549/513 |
| 2008/0281090 A1 | * | 11/2008 | Lee et al. | ...................... | 536/122 |
| 2010/0010185 A1 | | 1/2010 | Bowden et al. | | |

FOREIGN PATENT DOCUMENTS

WO   WO 2006071470   * 7/2006

OTHER PUBLICATIONS http://en.wikipedia.org/wiki/Citric_acid_cycle.*
http://en.wikipedia.org/wiki/Pyruvate_dehydrogenase.*
http://en.wikipedia.org/wiki/Isocitrate_dehydrogenase.*
http://en.wikipedia.org/wiki/Citric_acid_cycle (2011).*
http://en.wikipedia.org/wiki/Pyruvate_dehydrogenase (2011).*
http://en.wikipedia.org/wiki/Isocitrate_dehydrogenase (2011).*
Alberts et al. (Molecular Biology of the Cell 2nd Ed.,1989, Garland Publishing, Inc., 64-69).*
Bowden, N.B., seminar at the University of Iowa, Iowa City, IA, 16 pages, (Oct. 2007).
Bowden, N.B., "A Grignard reaction in water? New methods to carry out green cascade reactions using simple polymer thimbles", Department presentation at the University of Iowa, Iowa City, IA, 49 pages, (Nov. 2007).

(Continued)

*Primary Examiner* — Paul A Zucker
*Assistant Examiner* — Jennifer C Sawyer
(74) *Attorney, Agent, or Firm* — Viksnins Harris & Padys PLLP

(57) ABSTRACT

The invention provides methods and an apparatus useful for site-isolating reagents or catalysts during chemical reactions. The methods and apparatus are useful for carrying out cascade or domino reactions.

12 Claims, 12 Drawing Sheets

OTHER PUBLICATIONS

Miller, A. and N.B. Bowden, "A Materials Approach to the Dual-Site Isolation of Catalysts Bonded to Linear Polymers and Small, Ionic Molecules for Use in One-Pot Cascade Reactions", *Advanced Materials*, 20(21), 4195-4199 and 7 pages of supporting information, (2008).

Miller, A.L. and N.B. Bowden, "Site-isolation and recycling of $PdCl_2$ using PDMS thimbles", *J. Org. Chem.*, 74(13), 4834-40 and 12 pages of supporting information, (2009).

Mwangi et al., "'Pot-in-pot' reactions: Site isolation of organometallic catalysts and reagents for otherwise impossible cascade reasctions", *42nd Midwest Regional ACS Meeting*, Nov. 7-10, Kansas City KS, 9 pages, (2007).

Mwangi et al., "A materials approach to site-isolation of Grubbs catalysts from incompatible solvents and m-chloroperoxybenxoic acid", *Chemistry: a European Journal*, 14(22), 6780-6788 and 20 pages of supporting information, (2008).

Mwangi, M.T. and N.B. Bowden, "A new approach to cascade reactions using site-isolated catalysts and/or reagents", *8th International Symposium on Carbanion Chemistry (ISCC-8)*, University of Wisconsin, Madison, WI, 3 pages, (Jun. 6-10, 2007).

Mwangi, et al., "Occlusion of grubbs' catalysts in active membranes of polydimethylsiloxane: catalysis in water and new functional group selectivities", *J. Am. Chem. Soc.*, 128(45), 14434-14435 and 16 pages of supporting information, (2006).

Mwangi et al., "Sequential Reactions with Grubbs Catalyst and AD-mix-α/β Using PDMS Thimbles", *Org. Lett.*, 11(1), 33-36 and 24 pages of supporting information, (2009).

Peplow, M., "'Pot-in-a-pot' technique makes impossible cascade reactions easy", *Chemistry World*, 2 pages, (Apr. 10, 2008).

Runge et al., "Cascade Reactions Using $LiAlH_4$ and Grignard Reagents in the Presence of Water", *Angew. Chem. Int. Ed., 47*, 935-939 and 16 pages of supporting information, (2008).

Runge, et al., "New selectivities from old catalysts. Occlusion of Grubbs' catalysts in PDMS to change their reactions", *J. Organomet. Chem., 691*, 5278-5288, (2006).

\* cited by examiner

APPARATUS AND METHOD FOR CARRYING OUT MULTIPLE REACTIONS

PRIORITY OF INVENTION

This application claims priority under 35 U.S.C. §119(e) from U.S. Provisional Application No. 61/058,139, filed 2 Jun. 2008 and from U.S. Provisional Application No. 61/059,221, filed 5 Jun. 2008. Both applications are incorporated by reference herein in their entirety.

GOVERNMENT FUNDING

This invention was made with government support under 0734158 awarded by the National Science Foundation. The government has certain rights in the invention.

BACKGROUND OF THE INVENTION

The capability to carry out multiple reactions in one flask is an important goal in chemistry because of the need to speed the synthesis of molecules while producing less waste and requiring fewer hours of effort. These reactions are often called cascade or domino reactions; their names refer to how several reactions occur in a predicted sequence in the same reaction vessel. These reactions are examples of green chemistry because they require less solvent and produce less waste than the traditional method of isolating and characterizing products after each reaction. Numerous cascade reactions have been developed, and many of them use one catalyst that catalyzes multiple steps.

The use of single catalysts to carry out multiple reactions has been very successful, but these cascade reactions typically require the development of new catalysts and cannot be integrated with numerous homogeneous catalysts that are commercially available and are excellent catalysts for one reaction. The main reason for this limitation is that these catalysts often poison one another or are poisoned by reagents required by a second catalyst. Thus, only one can be added to a reaction vessel, and no cascade sequence is possible. What is needed to advance the field of cascade reactions is a new method to integrate multiple catalysts and reagents.

Because many catalysts and reagents poison one another, they must be site-isolated from each other, such that multiple catalysts or reagents can be integrated into one reaction vessel for cascade reactions. Site-isolation involves modifying the catalysts or reagents such that they do not come into contact and poison one another. Numerous methods for site-isolation exist, such as attachment to a polymer backbone, attachment of a catalyst to a solid polymeric support, attachment of catalysts to a heterogeneous surface, trapping a catalyst inside a zeolite cage, or using catalytic enzymes in which the active sites are protected by the enzyme from interacting with the active site of another enzyme. These methods have been very successful in some instances: for example, Frechet and Hawker attached both acidic and basic residues to the interiors of star polymers to integrate acid- and base-catalyzed reactions in one vessel. In another example, heterogeneous acidic and basic clays were added to the same reaction vessel to carry out concurrent acid- and base-catalyzed reactions.

One critical limitation that hinders current cascade reaction development is that most methods for site-isolation require the structure of the catalyst be altered for attachment to a polymer or solid support. These alterations may require several synthetic steps and affect the reactivity and selectivity of catalysts, or may simply not be possible with a wide variety of reagents.

SUMMARY OF THE INVENTION

A method for site-isolation of a reagent (e.g., a homogeneous, organometallic catalyst) from another reagent through the use of a selectively permeable physical barrier (e.g., a polymeric membrane) has been identified. This method does not require the structures of the catalyst or reagent to be altered and is a general method for site-isolation of a variety of catalysts and reagents without affecting their structures.

In one embodiment the invention provides a method comprising: converting one or more chemical reactants to a first product in a reaction vessel that is permeable to the first product; and optionally contacting the reaction vessel with a solution under conditions such that the first product passes out of the reaction vessel into the solution.

In one embodiment the invention provides an apparatus comprising: a first vessel to hold a first solution; and a second vessel including one or more selectively permeable (e.g. porous) walls to contact the first solution.

In one embodiment the invention provides a method comprising: contacting one or more reagents in a first vessel that comprises a porus material to provide a first reaction product that is capable of passing through the porous material into a second vessel.

In one embodiment the invention provides a method comprising: converting one or more chemical reactants in a reaction mixture to a product through the action of a catalyst that is substantially isolated from one or more catalyst deactivating components in the reaction mixture by a barrier that prevents the one or more catalyst deactivating components from coming into contact with the catalyst.

DETAILED DESCRIPTION

Selectively Permeable Materials

Figure 1:
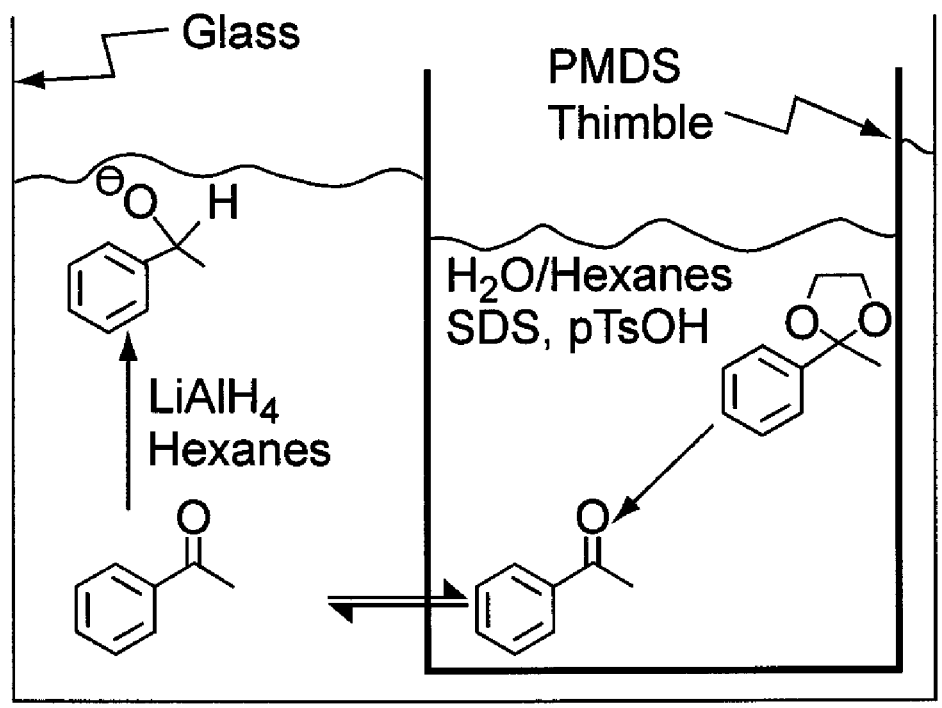
FIG. 1 illustrates an apparatus and a method of the invention.
Figure 1:
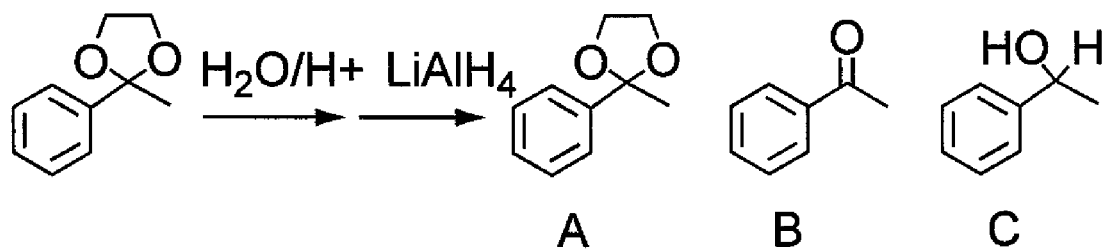

In one embodiment the invention provides a method comprising: converting one or more chemical reactants to a first product in a reaction vessel that is selectively permeable to the first product. Typically, the first vessel is made selectively permeable by incorporating a selectively permeable material into the walls of the vessel. Such a material can be selected based on the components that are intended to pass through the material (e.g. organic starting materials or reactants) and on the components that are not intended to pass through the material (e.g. a catalyst or a catalyst deactivating material).

According to the invention, a broad range of selectively permeable materials can be incorporated into the reaction vessels. For example, such materials can include polydimethylsiloxane, polymethelmetacrylate, cellulose, polyethylene, polypropylene, polystyrene, any polyamide or polyurethane, any polyacrylate, a derivative of polystyrene, polylactic acid, and polycaprolactone. One particular class of selectively permeable materials that can be incorporated into the reaction vessels is organic polymers such as polyurethanes and polydimethylsiloxane (PDMS). Another selectively permeable material that can be incorporated into the reaction vessels is polydicyclopentadiene.

In one embodiment of the invention the reaction vessel can be formed from a selectively permeable polymer such as PDMS. PDMS thimbles were used below to site-isolate incompatible reagents and perform cascade reactions. PDMS is a cheap, relatively inert, commercially available material that can be easily cast into reaction vessels with different sizes and shapes. This material has many beneficial properties for cascade reactions including its high flux rate towards many nonionic organic molecules that contrasts with the low flux rates of water and ionic molecules through PDMS. This difference in flux rates allows incompatible reagents to remain on the interior or exterior of PDMS thimbles for long time periods—they are site-isolated from each other. In particular cascade reactions, water was site-isolated from a consecutive set of reagents that are incompatible. In one embodiment, the methods of the invention are useful in the synthesis of organic molecules by cascade reactions, because they allow multiple reagents and catalysts to be used in cascade reactions without regard for whether they poison one another. One advantage of the methods of the invention is that ionic and polar reagents can be site-isolated from each other while organic molecules can pass through the barrier and react with both sets of reagents.

Encapsulation in PDMS vessels (e.g. thimbles) allows the catalyst to remain dissolved in an organic solvent, is amenable to reaction with polar or apolar substrates, and is a general method to site-isolate catalysts and reagents. The structures of the catalyst and the other reagents (e.g. MCPBA) are not altered. Thus methods of the invention allow for integration of organometallic catalysts and reagents that poison one another into cascade reactions without having to affect the structure of either catalyst or reagent.

Additionally, flux through the vessels can be varied by changing solvent, thickness of the selectively permeable materials, and temperature; this system may be tuned for each different set of reaction conditions. Using PDMS thimbles with thinner walls, the flux through PDMS can be increased while maintaining selectivity. The methods of the invention can be scaled up to an industrial scale through the use of many thimbles with optimum dimensions; their ease of fabrication will make new and varied thimbles easy to realize.

Catalysts

The methods of the invention allow for the use of a wide variety of catalysts in cascade reactions. For example, suitable catalysts include catalysts based on metals such as palladium, platinum, ruthenium, titanium, gold and mercury; acid catalysts (e.g. those that use acids such as HCl, sulfonic acid, or p-toluenesulfonic acid); base catalysts; and catalysts comprising one or more elements in columns 1-8 of the periodic table. In one embodiment of the invention, the catalyst is an organometalic catalyst. In another embodiment of the invention, the catalyst is a Grubbs catalyst. In one embodiment of the invention, the catalyst comprises palladium (e.g. $PdCl_2$).

Reactions

As detailed in the Examples hereinbelow, site-isolation can be used in conjunction with a wide variety of reactions, for example: deprotections, reductions, metathesis reactions, alkylations, epoxidations, aldol reactions, oxidations, and dihydroxylations.

Additionally, a wide variety of reagents can be site isolated using the apparatuses and the methods of the invention, for example: Grignard reagents, alkyl lithium reagents, lithium dialkyl cuprates, Grubbs' catalysts, meta-chloroperoxybenzoic acid, acids, bases, palladium chloride, and osmium dihydroxylation catalysts.

Solvents and Solutions

The solvents and solutions described herein include a broad range of polar and non-polar liquids. For example, the solvents and solutions can include one or more paraffins (e.g. n-pentane, n-hexane, hexanes, n-heptane, cyclopentane, cyclohexane, methylcyclopentane, and naphtha), isopars, halogenated hydrocarbons (e.g. chloroform, methylene chloride, carbontetrachloride, and the Freon class of halogenated solvents), ethers (e.g., tetrahydrofuran and di(C1-C6)alkylethers), gas phase solvents, supercritical $CO_2$, water, other ionic liquids (e.g. 1-butyl-3-methylimidazolium hexafluorophosphate), and other polar solvents.

Apparatus

Figure 9:
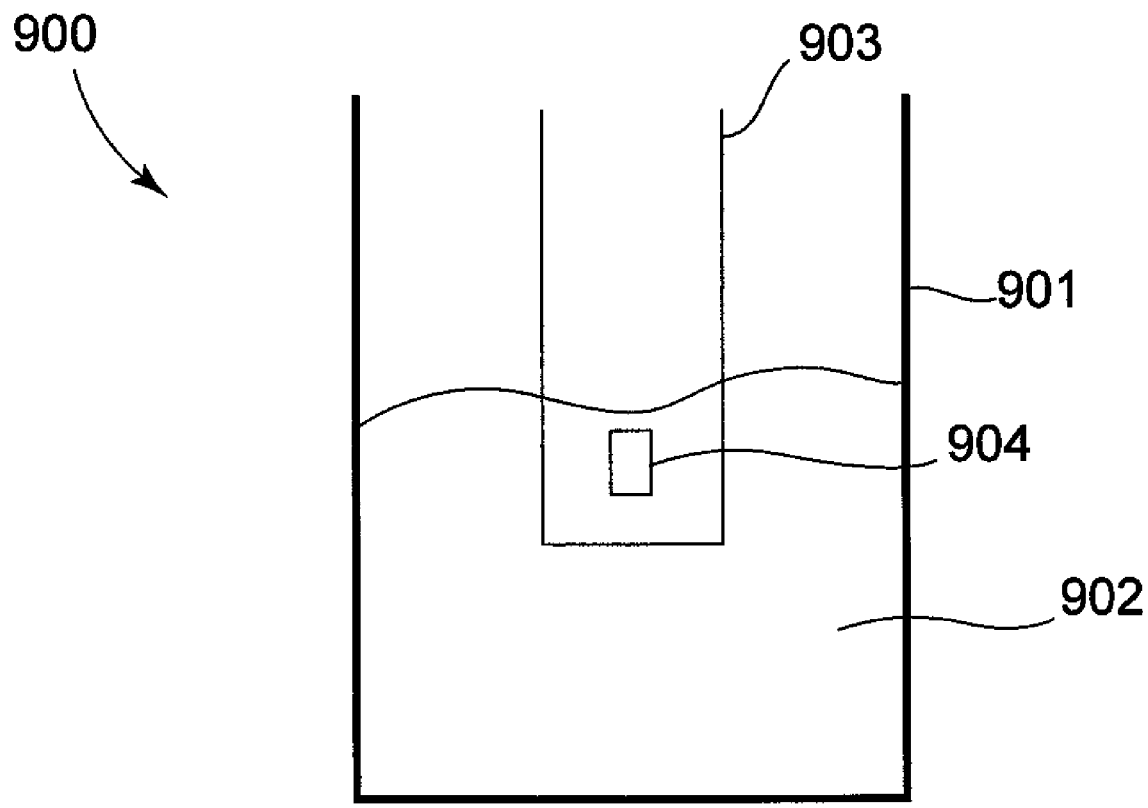
FIG. 9 illustrates an apparatus of the invention.

FIG. 9 shows an apparatus 900 including a first vessel 901 to hold a first solution 902 and a second vessel 903 including one or more selectively permeable walls 904 to contact the first solution 902. In one embodiment of the invention, the apparatus 900 is sealed to provide an inert environment. In one embodiment of the invention, the apparatus 900 is sealed and contains an inert gas such as, for example, argon. In one embodiment of the invention, the first vessel 901 is sealed to provide an inert environment. In one embodiment of the invention, the first vessel 901 is sealed and contains an inert gas such as, for example, argon. In one embodiment of the invention the first vessel 901 is suitable for carrying out a chemical reaction, for example, it is a beaker, thimble, flask or vial. In one embodiment of the invention the first vessel 901 is made of glass. In one embodiment of the invention the first vessel 901 is made of a selectively permeable material. In one embodiment of the invention, the solution 902 comprises one or more solvents. In one embodiment of the invention, the solution 902 comprises one or more solvents as described herein. In one embodiment of the invention, the solution 902 comprises one or more organic solvents (e.g. methylene chloride). In one embodiment of the invention, the solution 902 comprises one or more non-polar solvents. In one embodiment of the invention, the solution 902 comprises one or more polar solvents. In one embodiment of the invention, the solution 902 comprises water. In one embodiment of the invention, the solution 902 is water. In one embodiment of the invention, the second vessel 903 is sealed to provide an inert environment. In one embodiment of the invention, the second vessel 903 is sealed and contains an inert gas such as, for example, argon. In one embodiment of the invention, the second vessel 903 is selected from the vessels illustrated in FIGS. 10, 11, and 12. In one embodiment of the invention the second vessel 903 is made of glass. In one embodiment of the invention the second vessel 903 is made of a selectively permeable material. In one embodiment of the invention, the second vessel 903 contains one or more solvents. In one embodiment of the invention, the second vessel 903 contains one or more solvents as described herein. In one embodiment of the invention at least one of the selective permeable walls 904 comprises an organic polymer such as, for example, PDMS.

Figure 10:
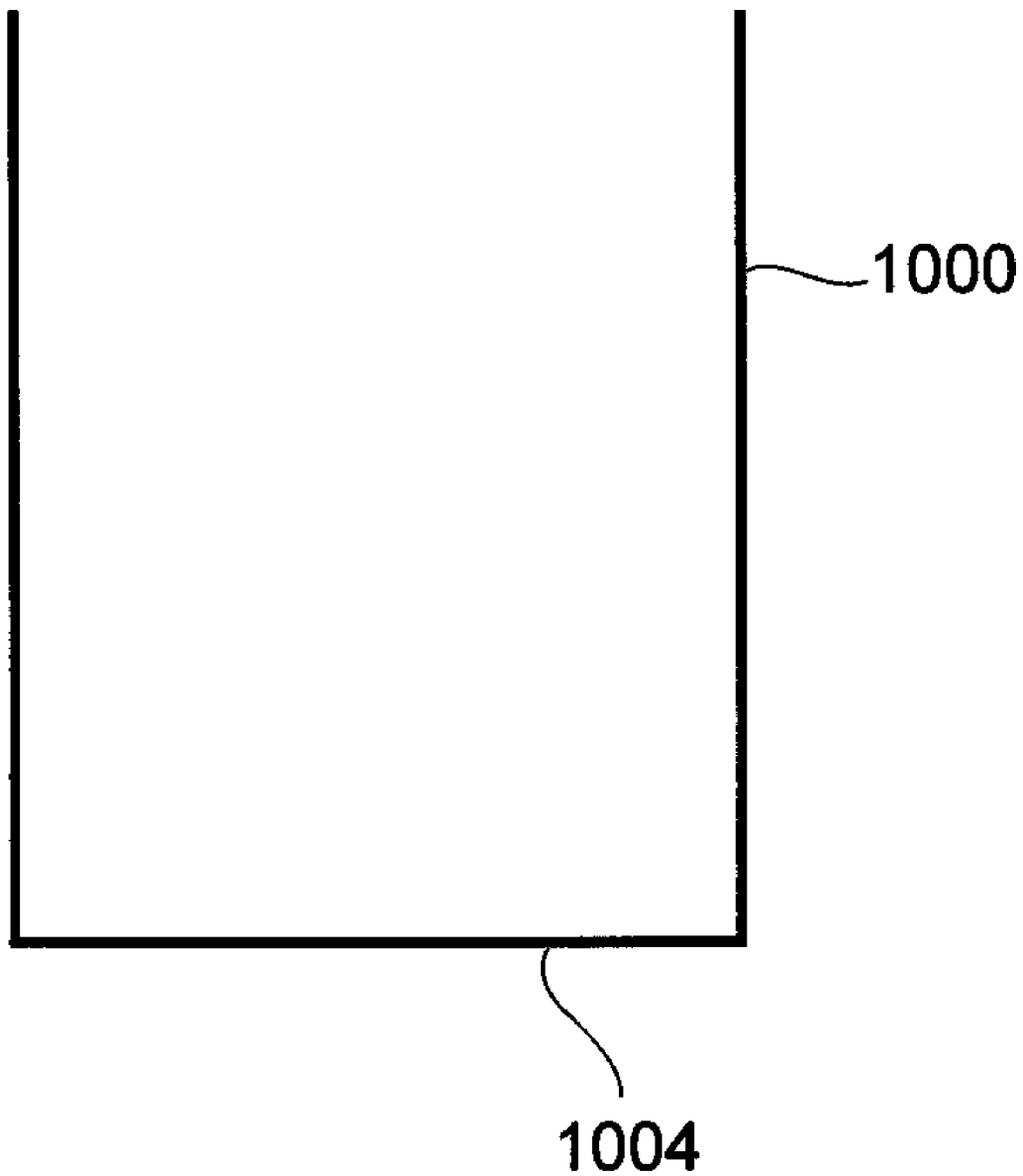
FIG. 10 illustrates a vessel.

FIG. 10 shows a vessel 1000 that is one embodiment of the vessel 903 (shown in FIG. 9), including a selectively permeable barrier 1004 that forms one side or portion of the vessel 1000. In one embodiment of the invention the selective permeable barrier 1004 comprises an organic polymer such as for example PDMS.

Figure 11:
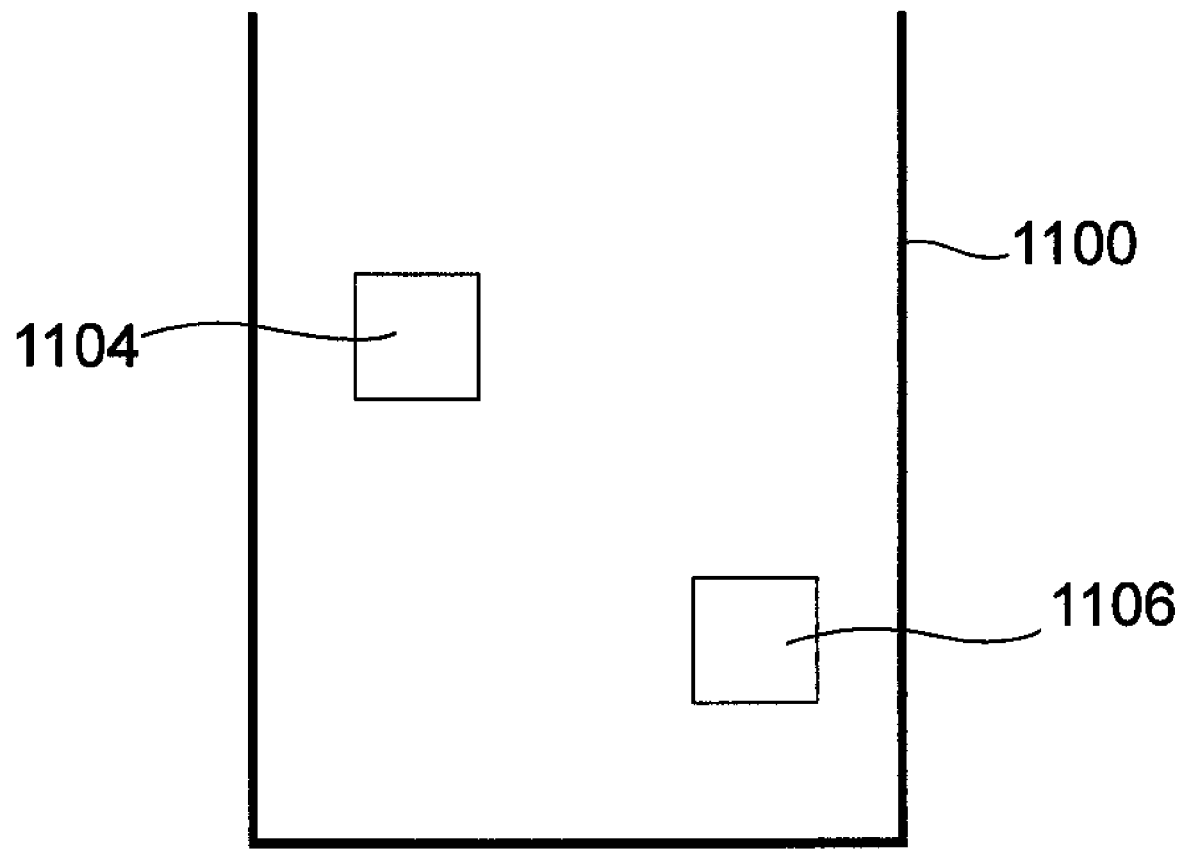
FIG. 11 illustrates an vessel.
Figure 12:
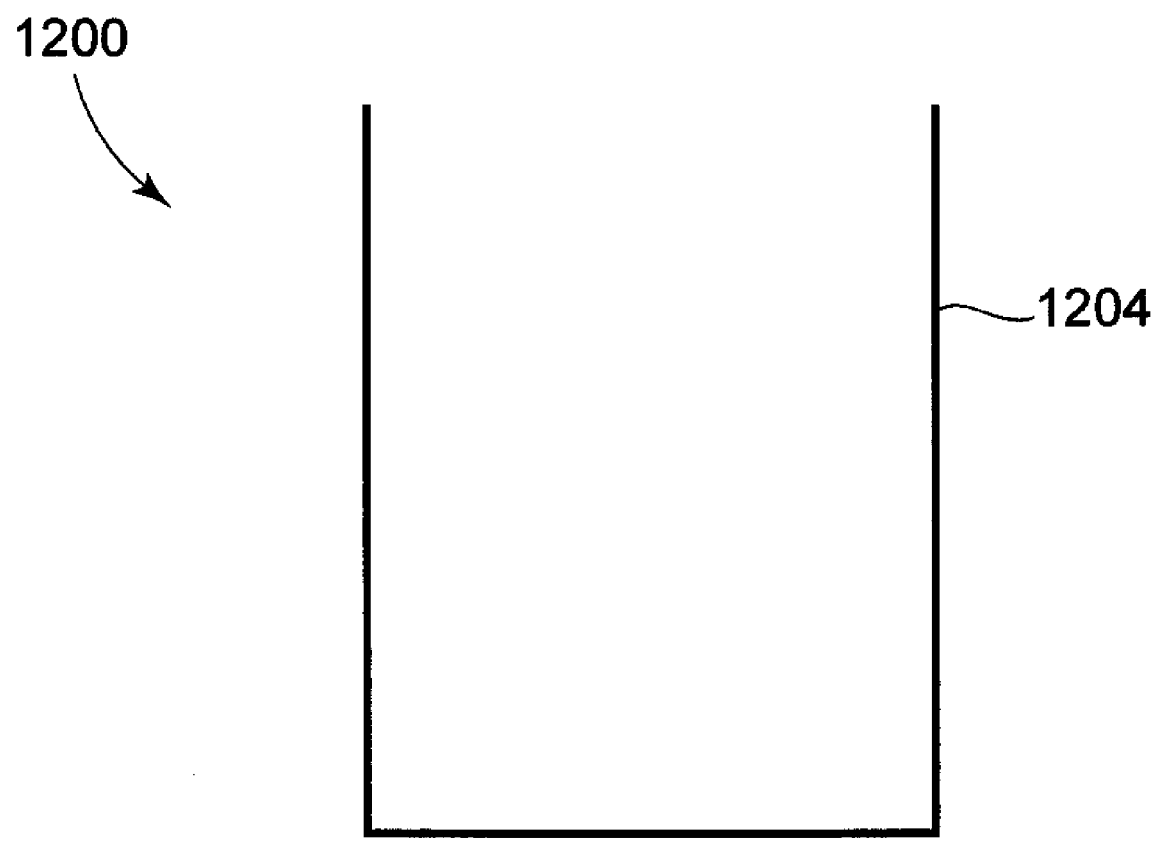
FIG. 12 illustrates a vessel.

FIG. 11 shows a vessel 1100 that is one embodiment of the vessel 903 (shown in FIG. 9), including two selectively permeable barriers 1104 and 1106. In one embodiment of the invention, each selectively permeable barrier 1104 and 1106 can optionally provide for the selective transmission of a different organic compound through the barrier. In one embodiment of the invention, each selectively permeable barrier 1104 and 1106 can optionally provide for the selective transmission of the same organic compound through the barrier. In one embodiment of the invention the selective permeable barriers 1104 and 1106 each comprise an organic polymer such as for example PDMS FIG. 12 shows a vessel 1200 that is one embodiment of the vessel 903 (shown in FIG. 9), that is formed from a selectively permeable material 1204. In one embodiment of the invention the selective permeable material 1204 comprises an organic polymer such as for example PDMS. In another embodiment of the invention, the vessel 1200 comprises a thimble such as the thimbles described in the Examples hereinbelow.

Specific Embodiments Of The Invention

The following non-limiting embodiments of the invention are provided to further illustrate the methods and apparatuses of the invention.

In one embodiment the invention provides a method comprising: deprotecting an acetal or a ketal to provide the corresponding aldehyde or ketone in a reaction vessel that is permeable to the aldehyde or ketone. This method can optionally further comprise: contacting the reaction vessel with a solution that comprises one or more solvents under conditions such that the aldehyde or ketone passes out of the reaction vessel into the solution; wherein the reaction vessel comprises a selectively permeable barrier that prevents the solution or one or more components in the solution from entering the reaction vessel. In one further embodiment of the invention the solution comprises a reagent that reacts with the aldehyde or ketone to provide a second product.

In one embodiment the invention provides a method comprising: cyclizing a diene with a metathesis reaction to provide the corresponding cyclic alkene in a reaction vessel that is permeable to the cyclic alkene. This method can optionally further comprise: contacting the reaction vessel with a solution that comprises one or more solvents under conditions such that the cyclic alkene passes out of the reaction vessel into the solution; wherein the reaction vessel comprises a selectively permeable barrier that prevents the solution or one or more components in the solution from entering the reaction vessel. In one further embodiment of the invention the solution comprises a reagent that reacts with the cyclic alkene to provide a second product.

In one embodiment the invention provides a method comprising: oxidizing an alkene with a catalyst that comprises palladium to provide the corresponding ketone, in a reaction vessel that is permeable to the ketone. This method can optionally further comprise contacting the reaction vessel with a solution that comprises one or more solvents under conditions such that the ketone passes out of the reaction vessel into the solution; wherein the reaction vessel comprises a selectively permeable barrier that prevents the solution or one or more components in the solution from entering the reaction vessel. In one further embodiment of the invention the solution comprises a reagent that reacts with the ketone to provide a second product.

In one embodiment the invention provides a method comprising: homocoupling an arylboronic acid with a catalyst that comprises palladium to provide the corresponding bisaryl homocoupling product in a reaction vessel that is permeable to the bisaryl homocoupling product. This method can optionally further comprise: contacting the reaction vessel with a solution that comprises one or more solvents under conditions such that the bisaryl homocoupling product passes out of the reaction vessel into the solution; wherein the reaction vessel comprises a selectively permeable barrier that prevents the solution or one or more components in the solution from entering the reaction vessel. In one further embodiment of the invention the solution comprises a reagent that reacts with the bisaryl homocoupling product to provide a second product.

The invention will now be illustrated by the following non-limiting Examples.

EXAMPLE 1

To illustrate the invention a cascade reaction was carried out wherein a cyclic ketal was deprotected to provide the corresponding ketone, followed by reduction of the ketone with $LiAlH_4$ to provide the corresponding alcohol. In a typical reaction, water (4 mL), an organic solvent (2 mL), sodium docecyl sulfate (0.2) as a detergent, and a cyclic acetal (0.5 g) were combined inside a PDMS thimble. Outside the PDMS thimble, an organic solvent (5 mL) and $LiAlH_4$ (0.145 g) were combined. The reaction was allowed to proceed for approximately 19 hours. Typically, over 50 equivalents of water to every molecule of $LiAlH_4$ were present, however, the PDMS barrier prevented the water and $LiAlH_4$ from reacting to a significant extent, while allowing for rapid diffusion of the ketone.

Initially, hexanes were used as the organic solvent to study the number of equivalents of $LiAlH_4$ that were needed to fully reduce the ketone (Table 1). The best results were obtained using 1.25 equivalents of $LiAlH_4$ for every equivalent of cyclic acetal. Although hexanes is a useful solvent because it swells PDMS and likely decreases the already slow diffusion of water through the PDMS by increasing the hydrophobicity of the membrane, many organic molecules have poor solubility in hexanes. To address this issue, other solvents were investigated.

Neat methylene chloride and THF were found to be less desirable, because they swelled PDMS and allowed water to diffuse through and quench the $LiAlH_4$. Accordingly, mixtures of these solvents with hexanes were investigated. Methylene chloride on the interior of the thimble and hexanes on the exterior of the thimble was a success and the isolated yield was 80%. Mixtures of methylene chloride or THF with hexanes gave incomplete conversions to the alcohol and suggested that diffusion of water to the exterior of the thimble was also a problem with these solvent mixtures.

TABLE 1

Solvent effect on the deprotection followed by reduction with $LiAlH_4$ in the presence of $H_2O$ as shown in FIG. 1.

| Solvent | $LiAlH_4$ equiv. | [a]Conversion (isolated yields) | | |
|---|---|---|---|---|
| | | A | B | C |
| Hexanes | 0.25 | 0 | 55 | 45 |
| Hexanes | 0.5 | 0 | 25 | 75 |
| Hexanes | 0.75 | 0 | 10 | 90 |
| Hexanes | 1.25 | 0 | 0 | 100 (89%) |
| [b]$CH_2Cl_2$/hexanes | 1.25 | 0 | 3 | 97 (80%) |
| $CH_2Cl_2$ | 1.25 | 0 | 100 | 0 |
| 25% $CH_2Cl_2$:75% hexanes | 1.25 | 0 | 20 | 80 |
| 50% $CH_2Cl_2$:50% hexanes | 1.25 | 0 | 15 | 85 |
| THF | 1.25 | 0 | 60 | 40 |

TABLE 1-continued

Solvent effect on the deprotection followed by reduction
with LiAlH₄ in the presence of H₂O as shown in FIG. 1.

| Solvent | LiAlH₄ equiv. | [a]Conversion (isolated yields) | | |
|---|---|---|---|---|
| | | A | B | C |
| 25% THF:75% hexanes | 1.25 | 5 | 15 | 80 |
| 50% THF:50% hexanes | 1.25 | 0 | 50 | 50 |

[a]The conversions were found by ¹H NMR spectroscopy of the crude reaction mixture. The isolated yields of selected products are shown in parentheses.
[b]Methylene chloride was the solvent on the interior of the thimble and hexanes was the solvent on the exterior of the thimble.

A two-step/one pot method to complete the same cascade sequence (FIG. 2) was explored. In this method, the solvents and reagents were added to the interior of the PDMS thimble and allowed to react for approximately 5 hours to deprotect the cyclic acetal. Next, solvent and LiAlH₄ were added to the exterior of the thimble to reduce the ketone to the alcohol over a period of 12 hours. The higher flux of the ketone relative to water through the PDMS thimble allowed the ketone to diffuse out of the thimble and be reduced to the alcohol before enough water diffused from the thimble to affect the conversion. The results in Table 2 demonstrate that although methylene chloride and THF were not useful solvents for this conversion by themselves, mixtures of each of these solvents with hexanes allowed the reaction to go to completion. Thus, this reaction sequence was found to be compatible with solvents that are commonly used in organic chemistry.

TABLE 2

Figure 2:
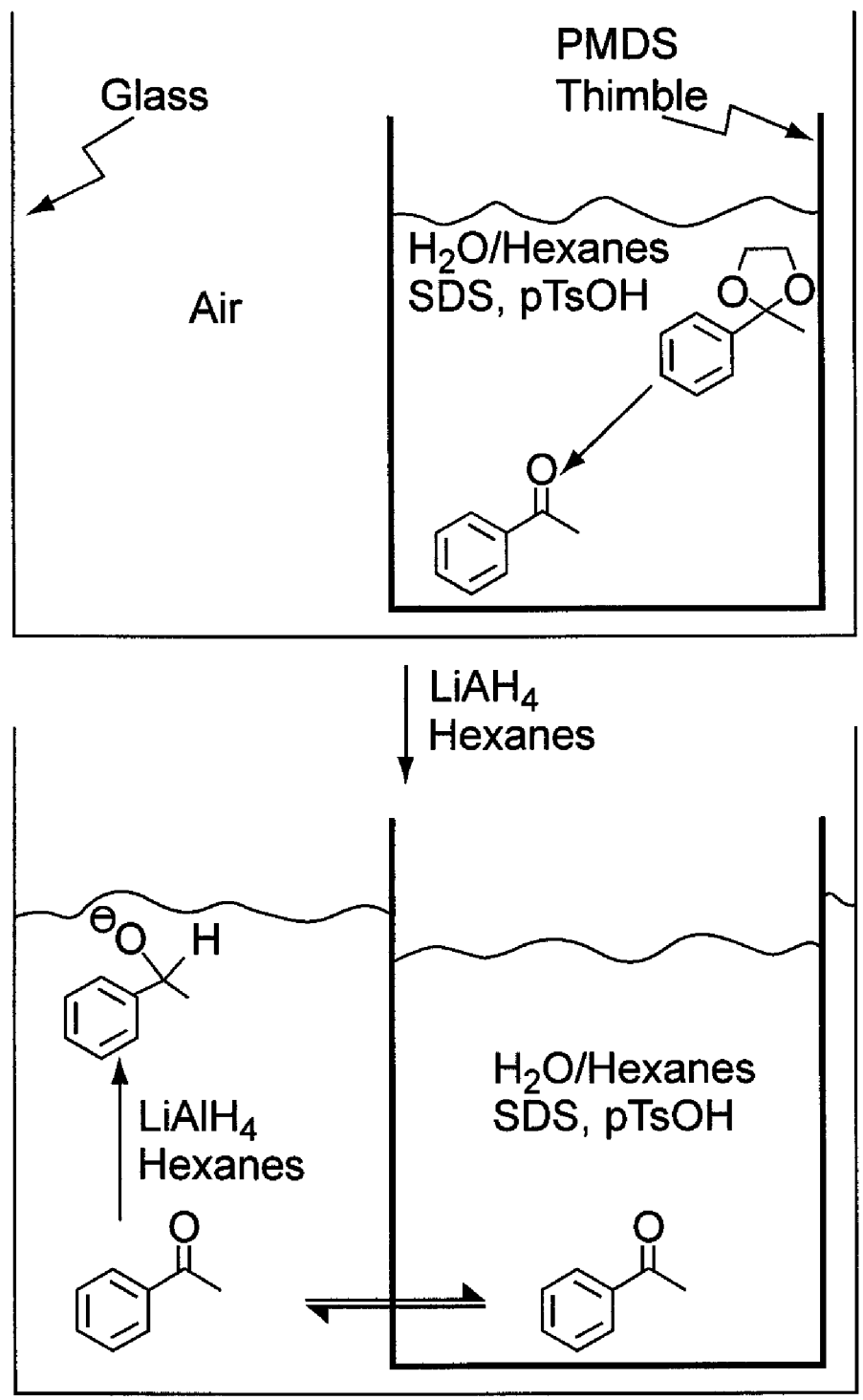
FIG. 2 illustrates an apparatus and a method of the invention.

Different solvents for the conversion of the cyclic acetal to
the alcohol using the two step/one pot sequence in FIG. 2.

| Solvent | [a]Conversion (isolated yields) | | |
|---|---|---|---|
| | A | B | C |
| 25% CH₂Cl₂:75% hexanes | 0 | 0 | 100 (86%) |
| 50% CH₂Cl₂:50% hexanes | 0 | 20 | 80 |
| CH₂Cl₂ | 0 | 90 | 10 |
| 25% THF:75% hexanes | 0 | 4 | 96 |
| 50% THF:50% hexanes | 0 | 4 | 96 (76%) |
| 75% THF:25% hexanes | 0 | 40 | 60 |
| THF | 0 | 70 | 30 |

[a]The conversions were found by ¹H NMR spectroscopy of the crude reaction mixture. The isolated yields of selected products are shown in parentheses.

Next the site-isolation of water from very reactive Grignard and alkyl lithium reagents (FIG. 3) was investigated. Due to the ionic bond in Grignard and alkyl lithium reagents their flux through PDMS was expected to be low in comparison to nonionic molecules. Typically, water (4 mL), hexanes (2 mL), a cyclic acetal (0.5 g), and sodium docecyl sulfate (0.2 g) were combined inside the thimble. After deprotection for 5 hours, 5 to 8 equivalents of the nucleophile were added to the exterior of the thimble and the reactions were monitored for 12 to 24 hours. As illustrated in Table 3 these reactions gave high yields of the tertiary alcohol despite the presence of over 10 equivalents of water for every Grignard reagent in the reaction vessel. Thus, it was demonstrated that water could successfully be site-isolated from alkyl lithium and Grignard reagents.

It was observed that the alkyl lithium and Grignard reagents reacted with PDMS, making it necessary to add them in excess. In fact, butyl lithium dissolved part of the PDMS membrane within 10 minutes to produce a hole. Although this reaction was able to reach 90% conversion, PDMS side products contaminated the reaction mixture. Grignard reagents were not as reactive towards the PDMS membrane as butyl lithium, but their effect was noticeable. After the reaction was completed the PDMS thimble was not as rubbery, and a white solid accumulated on the exterior of the thimbles during reactions with Grignard reagents.

As a result of the reactivity of alkyl lithium and Grignard reagents towards the PDMS thimbles, less reactive nucleophiles (e.g. lithium dialkyl cuprates) were also investigated. The cascade reaction with the cyclic ketal of acetophenone resulted in quantitative conversion to the aldol condensation product. Upon further study, it was determined that this reaction dominated even when acetophenone was added to the inside of the thimble in the absence of any water or acid and the cuprate was outside of the thimble.

To eliminate possibility of an aldol condensation, other reactions were carried out with the cyclic ketal of benzaldehyde. Reaction with the cuprate provided quantitative conversion to the secondary alcohol. Nonanone ketal was then studied to show that other substrates not as susceptible to enolate formation as acetophenone could be used with cuprates without undergoing aldol condensation reactions. Indeed, the tertiary alcohol was formed in high yields and no aldol condensation product was detected during the reaction with nonanone.

TABLE 3

Figure 3:
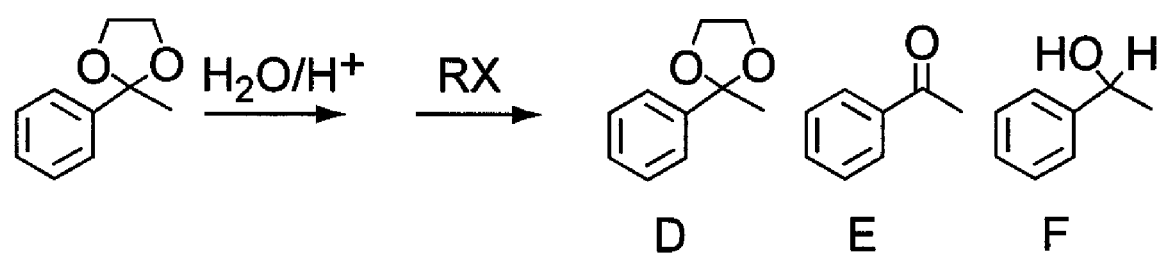
FIG. 3 illustrates a reaction sequence from Example 1.

Different cyclic ketals that we reacted by deprotection followed
by reaction with a variety of nucleophiles as shown in FIG. 3.

| [b]Ketal | [c]Nucleophile | [d]Time (h) | [a]Conversion (isolated yield) | | |
|---|---|---|---|---|---|
| | | | D | E | F |
| (phenyl dioxolane with methyl) | PhMgBr | 5/16 | 5 | 0 | 95 (93%) |

TABLE 3-continued

Different cyclic ketals that we reacted by deprotection followed
by reaction with a variety of nucleophiles as shown in FIG. 3.

| [b]Ketal | [c]Nucleophile | [d]Time (h) | [a]Conversion (isolated yield) D | E | F |
|---|---|---|---|---|---|
| 2-methyl-2-phenyl-1,3-dioxolane | 2-ethylhexyl-MgBr | 4/12 | 0 | 2 | 98 (81%) |
| 2-methyl-2-phenyl-1,3-dioxolane | allyl-MgBr | 5/14 | 0 | 2 | 98 (79%) |
| 2-methyl-2-phenyl-1,3-dioxolane | n-Bu-Li | 5/11 | 0 | 10 | 90 |
| 2-methyl-2-phenyl-1,3-dioxolane | Bu$_2$CuLi | 2/11 | 0 | 0 | [e]0 |
| 2-phenyl-1,3-dioxolane | Bu$_2$CuLi | 3.5/12 | 0 | 0 | 100 (87%) |
| 2,2-dibutyl-1,3-dioxolane | Bu$_2$CuLi | 12/22 | 2 | 2 | 96 (77%) |
| 2-methyl-2-(4-methoxybenzyl)-1,3-dioxolane | LiAlH$_4$ | 5/24 | 0 | 2 | 98 (84%) |

[a]The conversions were found by $^1$H NMR spectroscopy of the crude reaction mixture. The isolated yields of selected products are shown in parentheses.
[b]The solvent on the interior of the thimbles was hexanes but the solvent on the exterior of the thimbles varied. For the Grignard reagents it was diethyl ether, for butyl lithium and LiAlH$_4$ it was a mixture of diethyl ether and hexanes, and for the cuprates it was a mixture of diethyl ether and hexanes.
[c]Five to eight equivalents of nucleophile were added for every equivalent of cyclic acetal.
[d]The first number shows the time we allowed the deprotection to run before the addition of solvent to the exterior of the thimble. The second number is the time the reaction with the nucleophile was allowed to run before the reaction mixture was quenched.
[e]This reaction yielded the aldol condensation product.

Experimental Section

Fabrication of PDMS tubes: A glass vial (19 mm in diameter and 65 mm tall) was placed in a dessicator along with a few drops of trichloro(1H,1H,2H,2H-perfluorooctyl)silane and placed under static vacuum overnight. PDMS was prepared by mixing Sylgard 184 elastomer base (purchased from Dow Corning) and curing agent in a 10:1 ratio respectively and degassed for 30 minutes. The glass vials were dipped into the PDMS mixture and placed upside down in an oven at 65° C. for 30 minutes; this process was repeated once. PDMS was then allowed to cure overnight at 65° C. The top of the PDMS tube was cut with a razor blade around the cap of the vial and removed. A small amount of water was added to the inside of the vial and the cap replaced. The vial was then submerged in hexanes to swell the PDMS membrane at which point it delaminated from the glass vial. The PDMS thimbles were dried and used as is.

General Method 1: One-step cascade reaction procedure. 2-Methyl-2-phenyl-1,3-dioxolane (0.5 g, 3 mmol), sodium lauryl sulfate (0.2 g, 0.7 mmol) and a stir bar were added to the inside of a PDMS thimble. p-Toluene sulfonic acid monohydrate (0.145 g, 0.8 mmol) dissolved in 4 mL water was added to the inside of the PDMS thimble followed by 2 mL of hexanes. LiAlH$_4$ (0.145 g, 3.8 mmol) was added to the outside of the PDMS thimble followed by 5 mL hexanes. The reaction was stirred at room temperature for 19 hours. Water (5 mL) was added. The PDMS thimble was swelled with 20 mL hexanes and 2×20 mL diethyl ether. The organics were combined and dried over MgSO$_4$. The product was purified by flash chromatography.

General Method 2: Two step/one pot cascade reaction procedure. 2-Methyl-2-phenyl-1,3-dioxolane (0.5 g, 3 mmol), sodium lauryl sulfate (0.2 g, 0.7 mmol) and a stir bar were added to the inside of a PDMS thimble. p-Toluene sulfonic acid monohydrate (0.145 g, 0.8 mmol) dissolved in 4 mL of water was added to the inside of the PDMS thimble followed by 2 mL of 1:3 CH$_2$Cl$_2$:hexanes. The reaction was stirred for 5 hours at room temperature. LiAlH$_4$ (0.145 g, 3.8 mmol) was added to the outside of the PDMS thimble with 5 mL 1:3 CH$_2$Cl$_2$:hexanes. The reaction was stirred at room temperature for 17 hours. 5 mL of water was added. The PDMS thimble was swelled with 20 mL hexanes and 2×20 mL diethyl ether. The organics were combined and dried over MgSO$_4$. The product was purified by flash chromatography. Products were verified by comparison of $^1$H NMR spectra in literature.

Materials and Instrumentation:

Acetophenone, benzaldehyde, 5-nonanone, 4-methoxylphenylacetone, p-toluene sulfonic acid, ethylene glycol, sodium dodecyl sulfate, phenylmagnesium bromide, allylmagnesium bromide, 2-ethylhexylmagnsium bromide, copper (I) iodide, butyl lithium, lithium aluminum hydride, trichloro(1H,1H,2H,2H-perfluoroctyl)silane, and all organic solvents were purchased from Aldrich or Acros Organics at their highest purity. Sylgard 184 was purchased from Dow Corning. Geduran silica gel 60 was purchased from Fisher and used for all purifications. The ketals were synthesized from their respective ketones. Water was taken from the tap and used. $^1$H and $^{13}$C NMR spectra were recorded at 300 and 75 MHz respectively on a Bruker DPX 300 using CDCl$_3$. The solvent signal or TMS was used as the internal standard. $^1$H NMR spectra were compared to literature precedents.

Cascade Reactions:

Molecules previously synthesized and described in the literature were characterized by $^1$H and $^{13}$C NMR spectroscopy.

Preparation of 1-phenylethanol

2-Methyl-2-phenyl-1,3-dioxolane (0.5 g, 3 mmol), sodium dodecyl sulfate (0.2 g, 0.7 mmol) and a stir bar were added to the inside of a PDMS thimble. p-Toluene sulfonic acid monohydrate (0.145 g, 0.8 mmol) was dissolved in 4 mL water and added to the inside of the PDMS thimble followed by 2 mL of hexanes. LiAlH$_4$ (0.145 g, 3.8 mmol) was added to the outside of the PDMS thimble with 5 mL hexanes. The reaction was stirred at 25° C. for 19 hours. Water (5 mL) was added. The PDMS thimble was swelled with 20 mL hexanes and 2×20 mL diethyl ether. The organics were combined and dried over MgSO$_4$. The product was purified by column chromatography eluting with 1:4 ethyl acetate:hexanes to yield a colorless liquid (0.33 g, 89% yield). $^1$H NMR (CDCl$_3$): δ 1.44 (d, J=6.9 Hz, 3H), 2.42 (s, 1H), 4.81 (q, J=6.9 Hz, 1H), 7.22-7.33 (m, 5H). $^{13}$C NMR (CDCl$_3$): δ 25.05, 70.22, 125.31, 127.32, 128.37, 145.74.

Preparation of 1,1-diphenylethanol

2-Methyl-2-phenyl-1,3-dioxolane (0.5 g, 3 mmol), sodium dodecyl sulfate (0.2 g, 0.7 mmol) and a stir bar were added to the inside of a PDMS thimble. p-Toluene sulfonic acid monohydrate (0.145 g, 0.8 mmol) dissolved in 4 mL water was added to the inside of the PDMS thimble followed by 2 mL of hexanes. The reaction was stirred at 25° C. for 5 hours. Hexanes (15 mL) was added to the outside of the PDMS thimble followed by 8 mL of 3 M phenyl Grignard in diethyl ether (4.36 g, 24 mmol) and the reaction was stirred at 25° C. for 16 hours. Water (5 mL) was added. The PDMS thimble was swelled with 20 mL hexanes and 2×20 mL diethyl ether. The organics were combined and dried over MgSO$_4$. The product was purified by column chromatography, eluting with 1:9 ethyl acetate:hexanes. The product was recovered as a white solid (0.56 g, 93% yield). $^1$H NMR (CDCl$_3$): δ 1.93 (s, 3H), 2.25 (s, 1H), 7.22-7.41 (m, 10H). $^{13}$C NMR (CDCl$_3$): δ 30.83, 76.20, 125.81, 126.93, 128.14, 147.97.

Preparation of 4-ethyl-2-phenyloctan-2-ol

2-Methyl-2-phenyl-1,3-dioxolane (0.25 g, 1.5 mmol), sodium dodecyl sulfate (0.1 g, 0.35 mmol) and a stir bar were added to the inside of a PDMS thimble. p-Toluene sulfonic acid monohydrate (72.4 mg, 0.38 mmol) dissolved in 2 mL water was added to the inside of the PDMS thimble followed by 1 mL of hexanes. The reaction was stirred at 25° C. for 4 hours. Hexanes (2.5 mL) was added to the outside of the PDMS thimble followed by 12 mL of 1 M 2-ethylhexyl-magnesiumbromide (2.6 g, 12 mmol). The reaction was stirred for an additional 12 hours after which 5 mL water was added. The PDMS thimble was swelled with 20 mL hexanes and 2×20 mL diethyl ether. The organics were combined and dried over MgSO$_4$. The product was purified by column chromatography, eluting with 100% hexanes to yield a colorless oil (0.28 g, 80% yield). $^1$H NMR (CDCl$_3$): δ 0.68-0.86 (m, 6H), 1.08-1.29 (m, 9H), 1.57 (s, 3H), 1.63 (s, 1H), 1.70-1.75 (m, 2H), 7.19-7.46 (m, 5H). $^{13}$C NMR (CDCl$_3$): δ 10.43, 10.49, 14.00, 14.05, 22.86, 22.95, 26.95, 27.12, 28.48, 28.61, 30.45, 30.72, 33.82, 34.04, 34.62, 34.68, 47.99, 48.01, 75.07, 75.09, 124.82. 124.84, 126.27, 126.31, 127.88, 148.32, 148.38. HRMS: Calculated for C$_{16}$H$_{26}$O: 234.1984.

Preparation of 2-phenylpent-4-en-2-ol

2-Methyl-2-phenyl-1,3-dioxolane (0.5 g, 3 mmol), sodium dodecyl sulfate (0.2 g, 0.7 mmol) and a stir bar were added to the inside of a PDMS thimble. p-Toluene sulfonic acid monohydrate (0.145 g, 0.8 mmol) dissolved in 4 mL water was added to the inside of the PDMS thimble followed by 2 mL of hexanes. The reaction was stirred at 25° C. for 5 hours. Hexanes (5 mL) and 24 mL of 1 M allyl magnesiumbromide (3.49 g, 24 mmol) in diethyl ether was added to the outside of the PDMS thimble and the reaction was stirred for 14 hours. Water (5 mL) was added. The PDMS thimble was swelled with 20 mL hexanes and 2×20 mL diethyl ether and the organics were combined and dried over MgSO$_4$. The product was purified by flash chromatography eluting with 100% hexanes initially, increasing to 1:49 ethyl acetate:hexanes to yield a colorless oil (0.39 g, 79% yield). $^1$H NMR (CDCl$_3$): δ 1.54 (s, 3H), 2.09 (s, 1H), 2.49 (dd, J=13.8, 8.4 Hz, 1H), 2.68 (dd, J=13.5, 6.3 Hz, 1H), 5.09-5.16 (m, 2H), 5.55-5.66 (m, 1H), 7.21-7.26 (m, 1H), 7.31-7.36 (m, 2H), 7.41-7.45 (m, 2H). $^{13}$C NMR (CDCl$_3$): δ 29.86, 48.42, 73.58, 119.43, 124.72, 126.57, 128.13, 133.63, 147.59.

Preparation of 1-(4-methoxyphenyl)propan-2-ol 2-(4-Methoxybenzyl)-2-methyl-1,3-dioxolane (0.64 g, 3 mmol), sodium dodecyl sulfate (0.2 g, 0.7 mmol) and a stir bar were added to the inside of a PDMS thimble. p-Toluene sulfonic acid monohydrate (0.145 g, 0.8 mmol) dissolved in 4 mL water was added to the inside of the PDMS thimble followed by 2 mL of THF. The reaction was stirred at 25° C. for 5 hours. LiAlH$_4$ (0.229 g, 6 mmol) and 5 mL hexanes were added to the outside of the PDMS thimble and the reaction proceeded for 24 hours. 5 mL Water was added. The PDMS thimble was swelled with 20 mL hexanes and 2×20 mL diethyl ether, the organics were combined and dried over MgSO$_4$ and evaporated. The product was purified by flash chromatography eluting with 1:4 ethyl acetate:hexanes to yield a pale yellow oil (0.43 g, 83% yield). $^1$H NMR (CDCl$_3$): δ 1.22 (d, J=5.7 Hz, 3H), 1.69 (s, 1H), 2.61 (dd, J=13.2, 7.5 Hz, 1H), 2.72 (dd, J=13.5, 4.8 Hz, 1H), 3.78 (s, 3H), 3.93-3.98 (m, 1H), 6.85 (d, J=8.4, 2H), 7.12 (d, J=8.7 Hz, 2H). $^{13}$C NMR (CDCl$_3$): δ 22.61, 44.77, 55.18, 68.88, 113.89, 130.27, 130.43, 158.19.

Preparation of 1-phenylpentan-1-ol

Sodium dodecyl sulfate (0.2 g, 0.7 mmol), p-toluene sulfonic acid monohydrate (0.145 g, 0.8 mmol) and a stir bar were added to the inside of a PDMS thimble. All solvents were purged with Argon. Water (4 mL) was added to the inside of the PDMS thimble followed by 2 mL of THF. 2-phenyl-1,3-dioxolane (0.46 g, 3 mmol) was added to the inside of the PDMS thimble. The reaction was stirred at 25° C. for 3.5 hours. Separately, the cuprate was synthesized under N$_2$ utilizing standard Schlenk line techniques. CuI (2.88 g, 15 mmol) was placed in a Schlenk flask under N$_2$, 42 mL diethyl ether was added and the suspension was cooled in a brine bath for 20 minutes. 12 mL of 2.5 M BuLi (1.92 g, 30 mmol) in hexanes was added and the reaction was stirred for 30 minutes in the brine bath. The cuprate solution was then transferred to the outside of the PDMS thimble and the reaction proceeded for 12 hours. Water (5 mL) was added. The PDMS thimble was swelled with 3×20 mL diethyl ether, the organics were combined and dried over MgSO$_4$ and evaporated. The product was purified by flash chromatography eluting with 1:4 ethyl acetate:hexanes to yield a colorless oil (0.44 g, 87% yield). $^1$H NMR (CDCl$_3$): δ 0.89 (t, J=7.2 Hz, 3H), 1.21-1.42 (m, 4H), 1.66-1.84 (m, 3H), 4.66 (t, J=6.6 Hz, 1H), 7.25-7.36 (m, 5H). $^{13}$C NMR (CDCl$_3$): δ 14.02, 22.60, 27.99, 38.81, 74.71, 125.88, 127.48, 128.42, 144.92.

Preparation of 5-butylnonan-5-ol

Sodium lauryl sulfate (0.2 g, 0.7 mmol), p-toluene sulfonic acid monohydrate (0.290 g, 1.5 mmol) and a stir bar were added to the inside of a PDMS thimble and placed under N$_2$. All solvents were purged with Argon. H$_2$O (2 mL) was added to the inside of the PDMS thimble followed by 6 mL THF. 2,2-dibutyl-1,3-dioxolane was add and the reaction was stirred for 12 hours. Separately, the cuprate was synthesized under N$_2$ utilizing standard Schlenk line techniques. CuI (2.88 g, 15 mmol) was placed in a Schlenk flask under N$_2$, 26 mL diethyl ether was added and the suspension was cooled in a brine bath for 20 minutes. 12 mL of 2.5 M BuLi (1.92 g, 30 mmol) in hexanes was added and the reaction was stirred for 30 minutes in the brine bath. The cuprate solution was then transferred to the outside of the PDMS thimble and the reaction proceeded for 22 hours at 25° C. Water (5 mL) was added. The PDMS thimble was swelled with 3×20 mL diethyl ether, the organics were combined and dried over MgSO$_4$ and evaporated. The product was purified by flash chromatography eluting with 1:19 ethyl acetate:hexanes to yield a colorless oil (0.47 g, 77% yield). $^1$H NMR (CDCl$_3$): δ 0.89 (t, J=7.2 Hz, 9H), 1.3-1.43 (m, 18H), 3.58 (s, 1H). $^{13}$C NMR (CDCl$_3$): δ 14.07, 22.76, 27.83, 37.16, 71.99.

EXAMPLE 2

Figure 4:
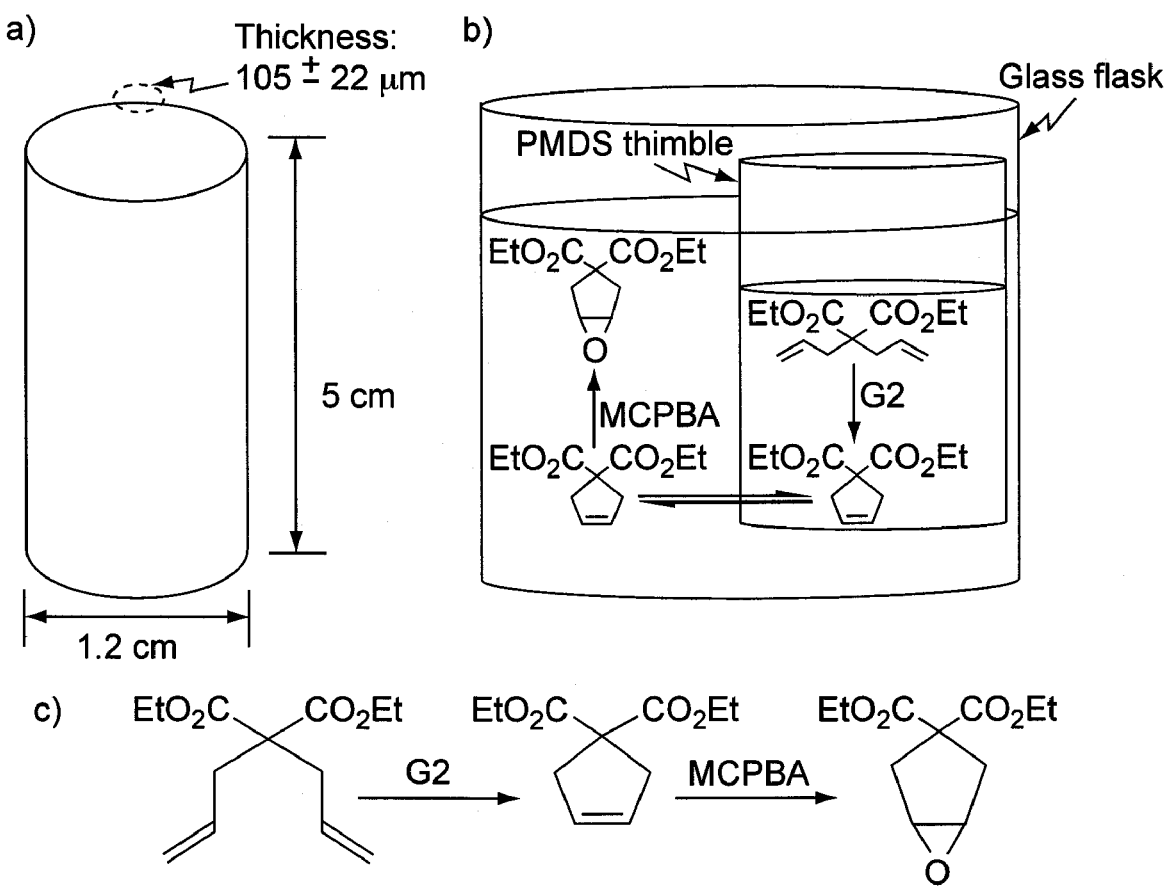
FIG. 4 illustrates a reaction sequence from Example 2 as well as an apparatus and a method of the invention.

Hollow PDMS thimbles were constructed that were 1.2 cm in diameter and 5 cm in height with PDMS walls that were 105 μm thick. The bottoms of these thimbles were composed of PDMS, but the tops were left open for easy filling with solvent and catalyst. Grubbs' catalyst was added to a solvent on the interior of the PDMS thimbles and MCPBA to the exterior of the thimbles. The Grubbs' catalysts and MCPBA poison each other even at low loadings of the Grubb's catalyst, but they were site-isolated by the PDMS walls while small molecules readily diffused through the walls to react with the catalyst and reagent. Thus, cascade reactions were possible with the Grubbs' catalyst and MCPBA even though these molecules were vastly incompatible with each other (FIG. 4).

Results and Discussion

Figure 5:
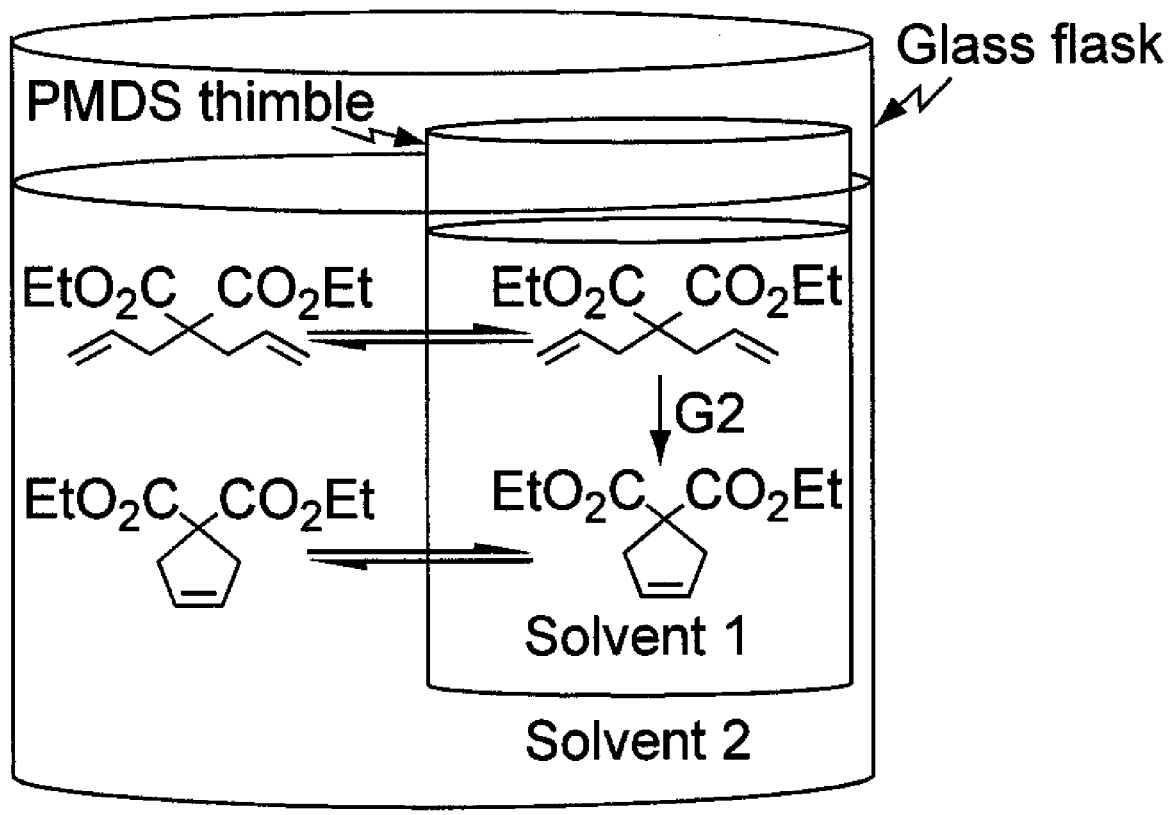
FIG. 5 illustrates a reaction sequence from Example 2 as well as an apparatus and a method of the invention.

A set of conditions was desired to site-isolate the Grubbs' catalysts on the interior of a PDMS thimble while allowing small molecules to diffuse from the exterior to the interior to react (FIG. 5). Specifically, a method was desired for adding reagents to the exterior of a PDMS thimble, having them diffuse into the thimble where the Grubbs' catalyst is dissolved, reacting with the Grubbs' catalyst, and diffusing out of the thimble while the Grubbs' catalyst remains encapsulated. It is necessary to keep the Grubbs' catalysts site-isolated on the interior of the thimbles (rather than allow them to diffuse through the PDMS) because this would allow a second reaction on the exterior of the thimble without concern for whether reagents on the exterior are poisoned by the Grubbs' catalyst.

Determining the optimum solvent for encapsulating Grubbs' catalysts in PDMS thimbles. Although a vast amount of literature on the rates of diffusion and the fluxes through PDMS for a variety of organic molecules exists, this data is incomplete for many of the molecules of interest and is not always directly applicable if PDMS is swelled by an organic solvent. Thus, the existing literature provides a helpful guide, but it is not possible to fully predict the correct solvent without measuring the flux for a given molecule of interest under different solvent conditions (FIG. 5).

Methylene chloride (CH$_2$Cl$_2$) and 1-butyl-3-methylimidazolium hexafluorophosphate [BMIM][PF$_6$] (a room temperature ionic liquid) were used as solvents for this reaction. Methylene chloride is a common solvent for the Grubbs' metathesis catalysts and swells PDMS well. [BMIM][PF$_6$] has been shown to be useful for metathesis reactions but it does not swell or diffuse into PDMS. This result is not surprising and can be understood on the basis of the incompatibility of the hydrophobic matrix of PDMS and the ionic character of [BMIM][PF$_6$]. By choosing these two sets of solvents, it was possible to test the effect of swelling PDMS on the rates of reaction and whether it affected the encapsulation of Grubbs' catalysts.

Table 4 shows the results for the reaction sequence shown in FIG. 5 using the Grubbs' first generation catalyst and different solvents. Because [BMIM][PF$_6$] does not swell PDMS, it was initially determined whether the diethyl diallylmalonate could diffuse into the interior of the thimble at a reasonable rate. From entries 1 and 2 in Table 4, it is clear that although the rate of diffusion is enhanced by heating, the conversions were low. An additional problem with this solvent was the poor solubility of the Grubbs' catalyst. [BMIM][PF$_6$] required a small amount of methylene chloride to be present to fully dissolve the catalyst. When methylene chloride was used, the catalyst rapidly diffused from the interior as seen by eye. The Grubbs' catalyst forms a red solution when dissolved in methylene chloride that, after reaction with a substrate resulting in the formation of a methylidene, becomes an orange solution. Because of these colors, it was obvious by eye whether the catalyst leached from the interior of the PDMS thimble. Different solvent mixtures of methylene chloride and [BMIM][PF$_6$] were tested and it was found that a 1/1 (v/v) mixture worked well.

TABLE 4

The effect of different solvents and temperatures on the ring closing metathesis of diethyl diallylmalonate as shown in FIG. 5.

| [a]Entry | [b]Solvent | Time (h) | Temp (° C.) | [c]Conversion (%) | [d]Leaching |
|---|---|---|---|---|---|
| 1 | [BMIM] | 72 | 25 | 5 | No |
| 2 | [BMIM] | 72 | 60 | 62 | No |
| 3 | $CH_2Cl_2$ | NA | 25 | [e]NA | Yes |
| 4 | 5/1 $CH_2Cl_2$/[BMIM] | 3 | 25 | 100 | Yes |
| 5 | 3/1 $CH_2Cl_2$/[BMIM] | 5 | 25 | 100 | Yes |
| 6 | 1/1 $CH_2Cl_2$/[BMIM] | 9 | 25 | 72 | No |
| 7 | 1/1 $CH_2Cl_2$/[BMIM] | 13 | 40 | 100 | No |
| [f]8 | 1/1 $CH_2Cl_2$/[BMIM] | 1 | 45 | 100 | No |

[a]Solvent on the interior (1.5 mL) and 4 mole % of the Grubbs' first generation catalyst were added to the interior of the thimble and the same solvent (4.0 mL) was added to the exterior.
[b][BMIM] is the abbreviation for [BMIM][PF$_6$]. The ratios are based on volumes.
[c]Conversion of the diethyl diallylmalonate to the cyclized product as determined by $^1$H NMR spectroscopy.
[d]Evidence for leaching of the Grubbs' catalyst from the interior of the thimble was monitored by eye using the color change of the solvent on the exterior of the thimble.
[e]The conversion was not found as the catalyst rapidly leached from the thimble.
[f]Grubbs' second generation catalyst was used.

To learn if the Grubbs' catalyst remained encapsulated, ring closing experiments were carried out as shown in FIG. 5 with a 1/1 (v/v) solvent mixture of $CH_2Cl_2$/[BMIM][PF$_6$] on the interior and exterior of the thimble. Every four hours an aliquot was removed from the exterior and analyzed to determine the concentration of Ru by inductively coupled plasma-mass spectrometry (ICP-MS). The results in Table 5 show that the Grubbs' catalyst remained mostly encapsulated, but it did leach to a small degree. To minimize the amount of catalyst that leached, a 1/1 (v/v) solvent mixture of MeOH/$H_2O$ on the exterior of the thimble was used and these experiments were repeated. This solvent mixture was chosen because the Grubbs' catalyst is insoluble in it. The results in Table 2 clearly demonstrate that over 99.5% of the catalyst remained encapsulated within the interior of the thimble even after 16 hours.

would remain encapsulated if MeOH/$H_2O$ was used as the solvent on the exterior of the thimbles. Accordingly, several reagents were allowed to react with encapsulated Grubbs' catalysts to determine if this choice of solvents was compatible with the method. The results in Table 6 show that these reactions were complete in reasonable times with good yields.

TABLE 6

Metathesis reactions with encapsulated catalyst dissolved in 1/1 (v/v) $CH_2Cl_2$/[BMIM][PF$_6$] and a solvent mixture of 1/1 (v/v) MeOH/$H_2O$ on the exterior of the thimble.

| Entry | Substrate | [a]Catalyst | Time (h) | [b]Yield (%) |
|---|---|---|---|---|
| 1 | EtO$_2$C, CO$_2$Et diallylmalonate | G2 | 2.5 | 93 |
| 2 | Ts-N diallyl | G2 | 2.5 | 87 |
| 3 | styrene | G2 | 19 | 84 |
| 4 | AcO-styrene | G2 | 26 | 69 |
| 5 | methylstyrene | G2 | 12 | 72 |

[a]These reactions were run at 4 mole % Grubbs' second generation catalyst at 45° C.
[b]Isolated yield after the reaction was complete.

Importantly, no color change of the MeOH/$H_2O$ was observed on the exterior of the thimble for even the longest

TABLE 5

Amount of Ru measured on the exterior of the PDMS thimbles as a function of time.

| | $CH_2Cl_2$/[BMIM][PF$_6$] on exterior | | | | MeOH/$H_2O$ on exterior | | | |
|---|---|---|---|---|---|---|---|---|
| Time (h) | [a][RU] (mg/mL) | [G2]$_{exterior}$ (mg/mL) | [b]$\frac{[G2]_{interior}}{[G2]_{exterior}}$ | [c]Total G2 in exterior (%) | [a][RU] (mg/mL) | [G2]$_{exterior}$ (mg/mL) | [b]$\frac{[G2]_{interior}}{[G2]_{exterior}}$ | [c]Total G2 in exterior (%) |
| 4 | 0.066 | 0.55 | 76 | 4.6 | 0.0040 | 0.034 | 1300 | 0.28 |
| 8 | 0.144 | 1.21 | 35 | 10.0 | 0.0069 | 0.058 | 740 | [d]0.41 |
| 12 | 0.154 | 1.30 | 32 | 10.7 | 0.0073 | 0.061 | 700 | [d]0.36 |
| 16 | 0.196 | 1.65 | 26 | 13.6 | 0.0092 | 0.077 | 560 | 0.36 |

[a]Measured by ICP-MS of a 0.5 mL aliquot taken from the exterior of the PDMS thimble.
[b]Ratio of the concentration of the Grubbs' catalyst on the interior to the exterior of the thimble.
[c]The percentage of the amount of catalyst added to the reaction that leached from the interior to the exterior of the thimble.
[d]The percentage was lowered from 8 to 12 h because of the removal of 0.5 mL of solvent from the exterior of the thimble to measure the concentration of Ru.

Figure 6:
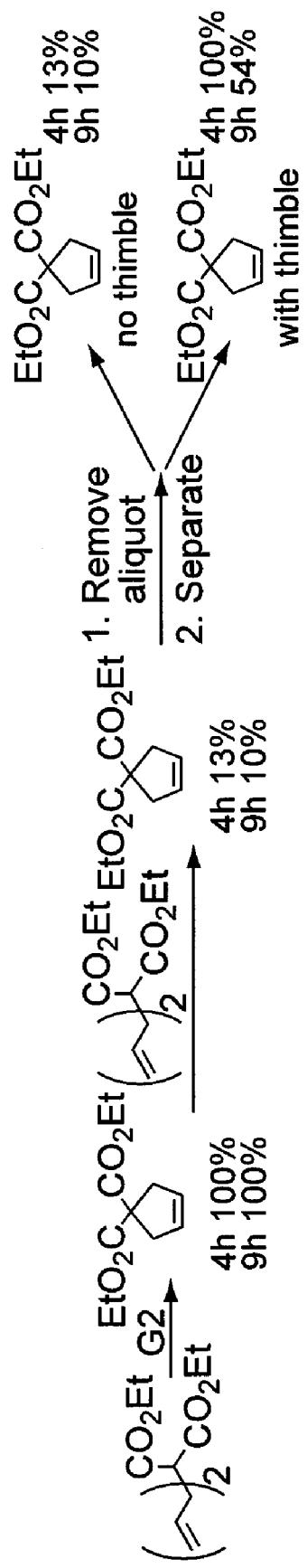
FIG. 6 illustrates a reaction sequence from Example 2 as well as an apparatus and a method of the invention.

Metathesis with 1/1 (v/v) $CH_2Cl_2$/[BMIM][PF$_6$] on the interior and 1/1 (v/v) MeOH/$H_2O$ on the exterior. The results in the prior section demonstrated that the Grubbs' catalyst reaction times. In addition, the ICP-MS experiments described in Table 5 demonstrated that less than 0.5% of the Ru leached to the exterior of the thimble after 16 hours, but whether it was active metathesis catalyst or not had to be determined. To answer this question, diethyl diallylmalonate was reacted with the Grubbs' second generation catalyst and $CH_2Cl_2$/[BMIM][$PF_6$] as the solvent on the interior of the thimbles and MeOH/$H_2O$ as the solvent on the exterior (FIG. 6).

Diethyl diallyl-malonate was added to the solvent on the exterior of the thimble and diffused through the PDMS walls to react. After 4 and 9 hours, the conversions on the exterior of the PDMS thimbles were determined to be 100%, and then we added another batch of diethyl diallylmalonate. The conversion was immediately measured on the exterior of the thimbles after the addition of diethyl diallylmalonate, and found to be approximately 10% and 13% for the two times. The low conversions reflect the fact that the diethyl diallylmalonate was added to the exterior of the thimbles and the product preferentially partitioned in the $CH_2Cl_2$/[BMIM][$PF_6$] found on the interior of the thimbles. Subsequently, 2 mL of solvent from the exterior of the thimbles was immediately removed and placed into a Schlenk flask under $N_2$. After 17 hours, conversions for the reactions carried out in the presence and absence of the PDMS thimbles were measured. The results indicate that little or no active metathesis catalyst was present in the solvent on the exterior of the thimbles after both 4 and 9 hours. Thus, although less than 0.5% of the Ru leached from the interior of the thimble, no active catalyst was found on the exterior. All of the metathesis reactions occurred within the thimble, even though the reagents were added to the exterior.

Cascade reactions with Grubbs' catalyst and MCPBA. To demonstrate the utility of the methods of the invention substrates were allowed to undergo metathesis on the interior of PDMS thimbles and epoxidations with MCPBA on the exterior of the thimbles. These two reactions were chosen because of the importance of metathesis reactions and epoxidations in organic chemistry. Evidence in the literature suggests that the Grubbs' catalyst and MCPBA are incompatible. For example, it has been shown that ruthenium compounds readily react with MCPBA to generate ruthenium oxo species. These species oxidize alkenes and alkanes even at low loadings of Ru. This made it reasonable to ask if the Grubbs' catalyst was stable in the presence of MCPBA and if it would catalytically poison MCPBA.

Control experiments demonstrated that the Grubbs' catalyst does poison MCPBA. Diethyl diallylmalonate was reacted with 4 to 0.1 mole % of Grubbs' second generation catalyst to yield the cyclized product and then MCPBA was added (Table 7). PDMS thimbles were not used so the Grubbs' catalyst was exposed to MCPBA. The metathesis reaction was first performed in 1 mL of $CH_2Cl_2$ and then 8 mL of MeOH with MCPBA was added. The conversions were poor even for the lowest catalyst loadings. Entry 4 is notable because there were 3,000 equivalents of MCPBA for every equivalent of Grubbs' catalyst; yet, the catalyst decomposed most of the MCPBA resulting in a conversion to epoxide of only 22%. Additional reactions were attempted where the cyclization was completed in a 1/1 (v/v) mixture of $CH_2Cl_2$/[BMIM][$PF_6$], followed by the addition of MCPBA dissolved in either MeOH or MeOH/$H_2O$. Again, a vigorous reaction between MCPBA and the Grubbs' catalyst was observed, and the epoxide was not seen by $^1$H NMR spectroscopy. These results demonstrate the incompatibility of even catalytic amounts of the Grubbs' catalyst with MCPBA.

TABLE 7

Control experiments to demonstrate that MCPBA is incompatible with the Grubbs' catalyst.

| Entry | [a]Solvent 1 | Solvent 2 | [b]G2 (Eq.) | [b]MCPBA (Eq.) | MCPBA/ G2 | [c]Epoxide (%) |
|---|---|---|---|---|---|---|
| 1 | $CH_2Cl_2$ (1 mL) | MeOH (8 mL) | 0.04 | 3 | 75/1 | <5 |
| 2 | | Same as above | 0.01 | 3 | 300/1 | <5 |
| 3 | | Same as above | 0.004 | 3 | 750/1 | 8 |
| 4 | | Same as above | 0.001 | 3 | 3000/1 | 22 |
| 5 | 1/1 $CH_2Cl_2$/BMIM | MeOH | 0.04 | 3 | 75/1 | <5 |
| 6 | 1/1 $CH_2Cl_2$/BMIM | 1/1 MeOH/$H_2O$ | 0.04 | 3 | 75/1 | <5 |

[a]In each of these reactions we added approximately 300 mg of the diethyl diallylmalonate and the indicated mole percent of Grubbs' catalyst to solvent 1 and reacted it for 4 h. Next, we added solvent 2 and the indicated equivalents (based on moles of diethyl diallylmalonate) of MCPBA and reacted it for 7 h.

[b]Equivalents based on diethyl diallylmalonate.

[c]The conversion of the epoxide was found by $^1$H NMR spectroscopy, the remaining cyclic olefin had not reacted.

Figure 7:
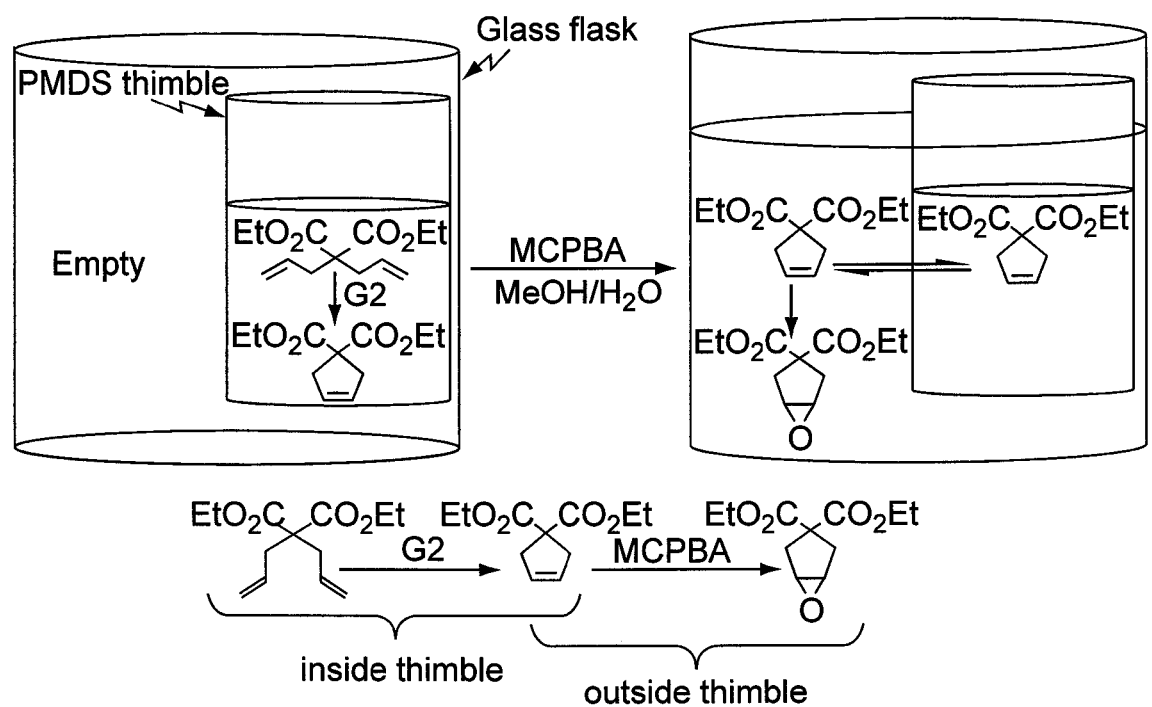
FIG. 7 illustrates a reaction sequence from Example 2 as well as an apparatus and a method of the invention.

To carry out the cascade reaction, a two-step sequence was used to minimize leaching of the Grubbs' catalyst from the PDMS thimble (FIG. 7). In these reactions, diethyl diallyl-malonate was added to the interior of the thimble containing 1 mL of 1/1 (v/v) CH$_2$Cl$_2$/[BMIM][PF$_6$] and the Grubbs' catalyst. After the metathesis reaction was complete, MCPBA was added in 8 mL of MeOH/H$_2$O to the exterior of the thimble, and the epoxidations were allowed to go to completion. The results for eight cascade reactions are shown in Table 8.

TABLE 8

Cascade reactions with a variety of reagents as shown in FIG. 4.

| Substrate | Product | [a]Time for metathesis (h) | [a]Time for epoxidation (h) | [b]Mole % G2 (MCPBA eq.) | [c]Yield (%) |
|---|---|---|---|---|---|
| 1 | | 4 | 12 | 4(3) | 71 |
| 2 | | 4 | 12 | 4(10) | 83 |
| 3 | | 6 | 14 | 4(5) | 83 |
| 4 | | 6 | 9 | 4(5) | 67 |
| 5 | | 5 | 11 | 4(5) | 68 |
| 6 | | 6 | 9 | 4(5) | 72 |

TABLE 8-continued

Cascade reactions with a variety of reagents as shown in FIG. 4.

| Substrate | Product | [a]Time for metathesis (h) | [a]Time for epoxidation (h) | [b]Mole % G2 (MCPBA eq.) | [c]Yield (%) |
|---|---|---|---|---|---|
| 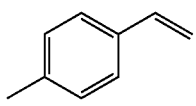 5 | 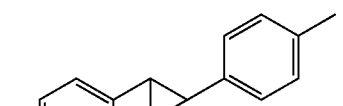 6 | 5 | 15 | 4(5) | 69 |

[a]These times refer to how long the metathesis and epoxidations reactions were allowed to run.
[b]The mole % of Grubbs' catalyst is shown and the equivalents of MCPBA based on the moles of diethyl diallylmalonate is shown in parenthesis.
[c]Isolated yields.

Recycling of the Grubbs' catalyst within a cascade sequence. A key aspect to any claim of site-isolation is that the catalyst can be recycled. The methods of the invention allow for recycling of a catalyst by merely removing the solvent on the exterior after the reaction is complete. To demonstrate this, the Grubbs' second generation catalyst, 1 mL of $CH_2Cl_2$, and diethyl diallylmalonate were added to the interior of a PDMS thimble. After one hour for the metathesis reaction, 20 mL of MeOH was added to the exterior of the thimble and removed after two hours. This procedure was repeated by the addition of more diethyl diallylmalonate to the interior of the thimble followed by 20 mL of MeOH to the exterior of the thimble. FIG. 8a shows that the conversions where quantitative, and the yields were high for five recycling steps. The amount of ruthenium present in the exterior of the thimble for each cycle was measured by ICP-MS. It was found that over 97% of the catalyst remained encapsulated within the thimble. To further demonstrate the importance of this method, the Grubbs' catalyst was recycled even as it was integrated into a cascade sequence with MCPBA (FIG. 8b). It is particularly noteworthy that high yields were obtained for these reactions even after several recycling steps. Thus, the Grubbs' catalyst can be recycled by simply removing the thimble from the reaction mixture, and this method is compatible with cascade reactions.

The data above illustrates a new, simple method to site-isolate homogeneous organometallic catalysts for use in cascade reactions and in reactions where it is desirable to recycle the catalyst. Although many useful homogeneous organometallic and inorganic catalysts have been developed over the preceding decades, they remain poorly integrated within cascade reactions because they are poisoned by each other or by other reagents. The methods of the invention allow such catalysts to be incorporated into cascade reactions without requiring a change in catalyst structure. Furthermore, site-isolation was accomplished via simple addition to a PDMS thimble. The methods of the invention are generally useful and can include the use of multiple catalysts or reagents straight from the manufacturer.

Experimental Section

Materials. Grubbs' first- and second-generation catalysts were purchased from Aldrich, stored in a glovebox under nitrogen, and used as supplied. Substrates and reagents were purchased from Acros/Fisher (diallylamine, 4-acetoxystyrene, 4-methoxystyrene, styrene, 4-vinylbenzylchloride, MCPBA, 1-chlorobutane, N-methylimidazole) or from Aldrich (diethyl diallylmalonate, 1,6-heptedien-4-ol) and used as supplied. Organic solvents (except the ionic liquid) were purchased from Acros or Aldrich at the highest purity and used as supplied. [BMIM][$PF_6$] was prepared according to literature procedures. All solvents used for metathesis reactions were degassed and maintained under nitrogen. Polydimethylsiloxane (PDMS) preparation kit (Sylgard 184) was purchased from Essex Brownell and used as supplied. Casting molds were made of brass. All reactions were performed under a nitrogen atmosphere using either Schlenk flasks or a glove box unless otherwise stated.

Characterization. $^1$H and $^{13}$C NMR spectra were recorded on a Bruker DPX 300 instrument using $CDCl_3$ as solvent and TMS as an internal standard. Leaching of ruthenium from the thimbles was determined by ICP-MS on a Varian Ultra mass 700 ICP-MS with sensitivity of 0.001 mg/mL at the University of Iowa hygiene laboratories.

Preparation of PDMS Thimbles. The two components from the PDMS kit were mixed in a ratio of 1/10 (w/w). The mixture was then degassed, placed in an oven maintained at 65° C. for about 5 min, and coated onto the brass rods. The PDMS was cured at 65° C. for 2 hours and the procedure was repeated once to yield tubes with thicknesses of 105±22 μm. Once cured, the tubes were cut and a bottom was added by placing a thin film of degassed, partially pre-cured PDMS onto a petri dish and allowing the tube to stand in the PDMS while it fully cured. The finished thimbles were then cut to the desired height, soaked in hexanes followed by methylene chloride, and dried before use. The thicknesses of the thimbles were measured using a calibrated Fisher Micromaster optical microscope interfaced to a computer using Micron1 imaging software.

General procedure for olefin metathesis reactions. Cyclopent-3-ene-1,1-dicarboxylic acid diethyl ester. In a glove box, Grubbs' second-generation catalyst (43 mg, 0.05 mmol) was placed in a PDMS thimble contained in a Schlenk flask. The flask was sealed, removed from the glove box, and placed under $N_2$. Solvent mixtures (1 mL of 1/1 (v/v) $CH_2Cl_2$/BMIM and 4 mL of 1/1 (v/v) MeOH/$H_2$O) were added to the interior and exterior of the thimble. Next, diethyl diallylmalonate (300 μL, 1.25 mmol) was added to the exterior of the thimble and the flask was placed in an oil bath maintained at 45° C. for 2.5 h. The reaction was cooled to room temperature and product extracted with 3×10 mL hexanes. The hexane extracts were dried over anhydrous $MgSO_4$, solvent was removed in vacuo, and the product was purified by passing through a silica gel column eluting with 5% EtOAc in hexanes to give the title compound as a light yellow liquid (0.25 mg, 1.16 mmol, 93% yield).

Procedure for cascade reactions. Diethyl 6-oxa-bicyclo[3.1.0]hexane-3,3-dicarboxylate, 1. In a glove box, Grubbs' second generation catalyst (43 mg, 0.05 mmol) was placed in a PDMS thimble contained in a Schlenk flask. The flask was sealed, removed from the glove box, and placed under $N_2$. Solvent (1 mL of 1/1 $CH_2Cl_2$/[BMIM][$PF_6$]) was added on the interior of the thimble followed by diethyl diallylmalonate (300 µL, 1.25 mmoles). The reaction mixture was allowed to stir at ambient conditions for 3 hours after which the flask was slowly charged with MCPBA (1 g, 3.7 mmole in 8 mL of 1/1 (v/v) MeOH/water) on the exterior of the thimble and allowed to continue stirring for a further 12 hours. Solvent on the exterior of the thimble was removed and washed repeatedly with saturated $NaHCO_3$ and extracted using 3×10 mL $CH_2Cl_2$. Thimble contents were extracted with 10 mL of hexanes. The hexane and DCM extracts were pooled, washed with brine, and dried over anhydrous $MgSO_4$. Solvent was then removed in vacuo and the product was purified using a silica gel column eluting with 10% EtOAc to give the target epoxide in 71% yield (0.203 g, 0.89 mmoles).

Control experiments to demonstrate that the metathesis reaction was occurring on the interior of the PDMS thimbles (FIG. 6). In a glove box, Grubbs' second-generation catalyst (43 mg, 0.05 mmol) was placed in a PDMS thimble contained in a Schlenk flask. The flask was sealed and removed from the glove box. While maintaining under nitrogen using a Schlenk line, 1 mL of 1/1 DCM/[BMIM][$PF_6$] was added to the interior of the thimble while 4 mL of 1/1 MeOH/$H_2O$ was added to the flask on the exterior of the thimble. Next, diethyl diallylmalonate (300 µL, 1.25 mmoles) was added to the exterior of the thimble and the flask was placed in an oil bath maintained at 45° C. for 4 hours. An aliquot was removed, extracted with hexanes, and the hexanes extracts were dried over anhydrous $MgSO_4$ and concentrated in vacuo. The sample was analyzed by $^1H$ NMR spectroscopy to determine the conversion. Fresh diethyl diallylmalonate (300 µL, 1.25 mmol) was added to the exterior of thimble and mixed thoroughly for about 2 minutes after which aliquot was removed and analyzed by NMR spectroscopy as detailed above. Next, half of the remaining solvent from the exterior of thimble was transferred by syringe to a Schlenk flask under $N_2$. Both flasks were heated at 45° C. for 14 hours after which they were analyzed for conversion using $^1H$ NMR spectroscopy.

Control experiments to demonstrate that Grubbs' metathesis catalyst poisons MCPBA. In a glove box, a stock solution of Grubbs' second generation catalyst was prepared (39 mg in 10 mL $CH_2Cl_2$). An aliquot of the stock solution (280 µL, 1.09 mg, 0.013 mmol) was added to a Schlenk flask and further diluted with 720 µL of $CH_2Cl_2$. The flask was sealed, removed from the glove box and attached to a Schlenk line. Diethyl diallylmalonate (300 µL, 1.25 mmol) was added, and the reaction was maintained at room temperature for 4 hours. The flask was then charged with MeOH (8 mL) and MCPBA (0.92 g, 3.75 mmol). This reaction was allowed to stir for 7 hours, after which an aliquot was analyzed by $^1H$ NMR spectroscopy to determine conversion to the epoxide. Similarly, this procedure was repeated for different solvent mixtures and different ratios of Grubbs' second-generation catalyst to MCPBA as summarized in Table 7.

Figure 8:
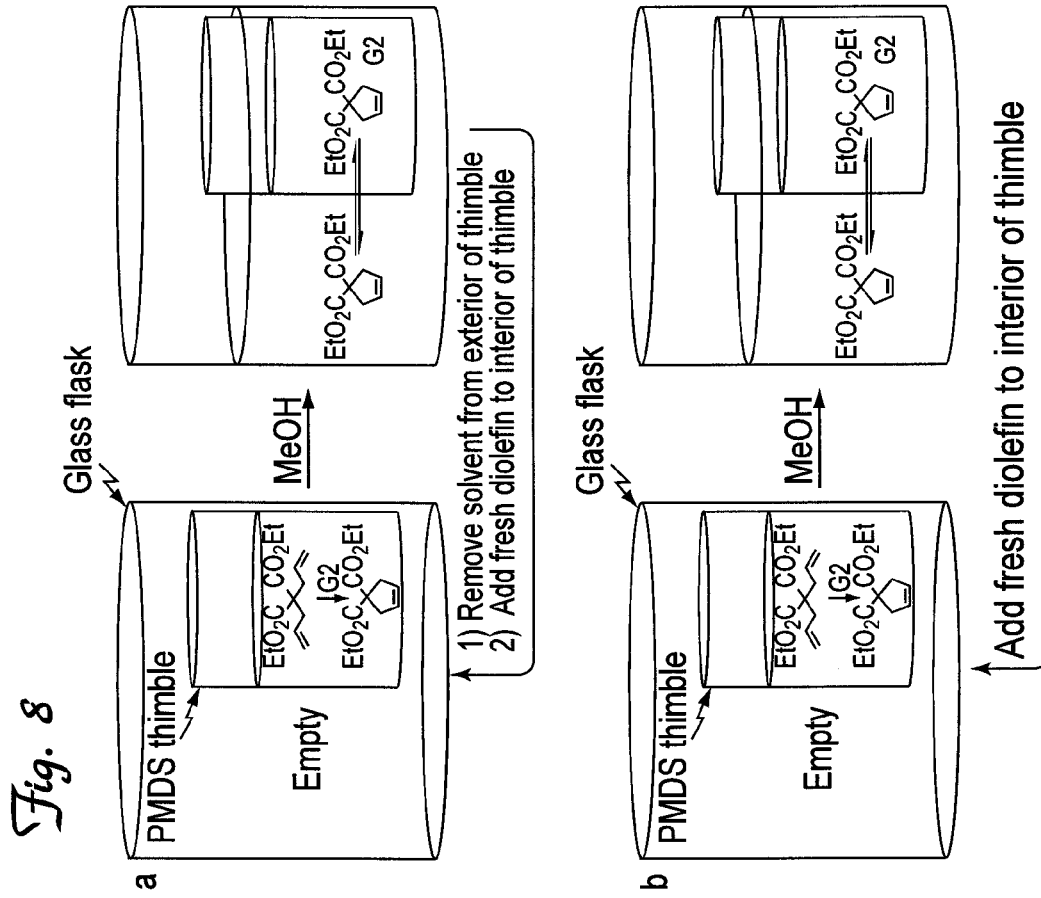
FIG. 8 illustrates a reaction sequence from Example 2 as well as an apparatus and a method of the invention.

Procedure for recycling encapsulated Grubbs' second generation catalysts (FIG. 8). In a glovebox, Grubbs' second generation catalyst (53 mg, 0.06 mmol) was placed in a PDMS thimble contained in a Schlenk flask. The flask was sealed, removed from the glove box, and placed under $N_2$. To the thimble was added 1 mL of $CH_2Cl_2$ followed by diethyl diallylmalonate (300 µL, 1.25 mmol). This mixture was allowed to stir at ambient temperature under $N_2$. After 1 hour, 20 mL of MeOH was added to the exterior of the thimble. After 2 hours, all the solvent on the exterior of thimble was removed, concentrated in vacuo, and weighed. Conversions were determined by $^1H$ NMR spectroscopy. Fresh diethyl diallylmalonate (300 µL, 1.25 mmol) was added to the interior of the thimble. This procedure was repeated for a total of 6 cycles.

Procedure for recycling encapsulated Grubbs' second generation catalysts within a metathesis/epoxidation cascade sequence. The catalyst was recycled as described above except that for each cycle, the solvent on the exterior of the thimble was removed and placed in a new flask containing MCPBA (0.92 g, 3.74 mmole). The epoxidation reaction was allowed to run for 12 hours. Conversion of the ring closed olefin to the epoxide was confirmed to be >98% by $^1H$ NMR spectroscopy. The reaction mixture was then dissolved in 50 mL $CH_2Cl_2$ and washed with 100 mL water followed by 3×50 mL saturated sodium bicarbonate. The organic extract was dried over anhydrous $MgSO_4$ and concentrated in vacuo. The product was purified by column chromatography using 10% EtOAC in hexanes as the eluant. This procedure was repeated for a total of five cycles.

General procedure for olefin metathesis reactions. Cyclopent-3-ene-1,1-dicarboxylic acid diethyl ester. In a glove box, Grubbs' second generation catalyst (43 mg, 0.05 mmole) was placed in a PDMS thimble contained in a Schlenk flask. The flask was sealed, removed from the glove box, and placed under $N_2$. Solvent mixtures (1 mL of 1/1 $CH_2Cl_2$/BMIM and 4 mL of 1/1 MeOH/$H_2O$) were added to the interior and exterior of the thimble. Next, diethyl diallylmalonate (300 µL, 1.25 mmoles) was added to the exterior of the thimble and the flask was placed in an oil bath maintained at 45° C. for 2.5 h. The reaction was cooled to room temperature and product extracted with 3×10 mL hexanes. The hexane extracts were dried over anhydrous $MgSO_4$, solvent was removed in vacuo, and the product was purified by passing through a silica gel column eluting with 5% EtOAc in hexanes to give the title compound as a light yellow liquid (0.25 mg, 1.16 mmoles, 93% yield). The $^1H$ and $^{13}C$ NMR data matched literature values. $^1H$ NMR ($CDCl_3$): δ 1.26 (t, 6H, J=7.2 Hz), 3.02 (br s, 4H), 4.21 (q, 4H, J=7.2 Hz), 5.61 (br s, 2H). $^{13}C$ NMR ($CDCl_3$): δ 13.59, 40.38, 58.33, 61.04, 127.36, 171.68.

N-Tosyl-2,5-dihydropyrolle. Reaction of N,N-diallyl tosylamine with Grubbs' second generation catalyst for 2 hours gave the title compound in 83% yield. The $^1H$ and $^{13}C$ NMR spectra agreed with those reported in the literature. $^1H$ NMR ($CDCl_3$): δ 2.44 (s, 3H), 4.13 (s, 4H), 5.66 (s, 2H), 7.33 (d, 2H, J=7.8 Hz), 7.71 (d, 2H, J=7.8 Hz). $^{13}C$ NMR ($CDCl_3$): δ 21.52, 54.83, 125.43, 127.40, 129.75, 134.21, 143.42.

(E)-Stilbene. Reaction of styrene with Grubbs' second generation catalyst for 19 hours gave the title compound in 94% yield. The 1H and $^{13}C$ NMR spectra agreed with those reported in the literature. $^1H$ NMR ($CDCl_3$): δ7.11 (s, 2H), 7.25 (tt, 2H, J=7.2, 1.2 Hz), 7.34 (m, 4H), 7.50 (m, 4H) $^{13}C$ NMR ($CDCl_3$): δ126.51, 127.62, 128.65, 128.68, 137.28.

(E)-4,4'-Acetoxystilbene. Reaction of 4-acetoxystyrene with Grubbs' second generation catalyst for 5 hours gave the title compound in 80% yield. The $^1H$ and $^{13}C$ NMR spectra agreed with those reported in the literature. $^1H$ NMR ($CDCl_3$): δ2.32 (s, 6H), 7.04 (s, 2H), 7.08 (d, 4H, J=8.4 Hz), 7.51 (d, 4H, J=8.4 Hz) $^{13}C$ NMR ($CDCl_3$): δ21.15, 121.81, 127.40, 127.87, 134.96, 150.07, 169.46. HRMS: calculated for $C_{16}H_{16}O_4$ 296.1049, Found: 296.1052.

(E)-4,4'-Dimethylstilbene. Reaction of 4-methylstyrene with Grubbs' second generation catalyst for 8.5 hours gave the title compound in 76% yield. The $^1H$ and $^{13}C$ NMR spectra agreed with those reported in the literature. $^1H$ NMR ($CDCl_3$): δ2.34 (s, 6H), 7.03 (s, 2H), 7.14 (d, 4H, J=7.8 Hz), 7.39 (d, 4H, J=7.8 Hz) $^{13}C$ NMR ($CDCl_3$): δ21.22, 126.29, 127.62, 129.34, 134.72, 137.23.

Procedure for metathesis-epoxidation cascade reactions. Diethyl 6-oxa-bicyclo[3.1.0]hexane-3,3-dicarboxylate. In a glove box, Grubbs' second generation catalyst (43 mg, 0.05 mmole) was placed in a PDMS thimble contained in a Schlenk flask. The flask was sealed, removed from the glove box, and placed under $N_2$. Solvent (1 mL of 1/1 $CH_2Cl_2$/BMIM) was added to the interior of the thimble followed by diethyl diallylmalonate (300 μL, 1.25 mmoles). The reaction mixture was allowed to stir at ambient conditions for 3 hours after which the flask was slowly charged with MCPBA (1 g, 3.7 mmole in 8 mL of 1/1 MeOH/water) on the exterior of the thimble and allowed to continue stirring for a further 12 hours. Solvent on the exterior of the thimble was removed, washed repeatedly with saturated $NaHCO_3$, and extracted using 3×10 mL $CH_2Cl_2$. Thimble contents were extracted with 10 mL of hexanes. The hexane and $CH_2Cl_2$ extracts were pooled, washed with brine, and dried over anhydrous $MgSO_4$. Solvent was then removed in vacuo and the product was purified using a silica gel column eluting with 10% EtOAc in hexanes to give the target epoxide in 71% yield (0.203 g, 0.89 mmoles). $^1$H NMR ($CDCl_3$): δ 1.21-1.30 (overlapping triplets, 6H), 2.20 (d, 2H, J=14.7 Hz), 3.03 (d, 2H, J=14.7 Hz), 3.53 (s, 2H), 4.15-4.22 (2 overlapping quartets, 4H). $^{13}$C NMR ($CDCl_3$): δ 13.80, 13.82, 31.43, 35.70, 55.36, 55.61, 61.48, 61.82, 170.76, 171.06. HRMS (m/z): Calcd for $C_{11}H_{16}O_5$: 228.0998; found, 228.0998.

trans-Stilbene oxide. Reaction of styrene with Grubbs' second generation catalyst for 6 hours, followed by reaction of the subsequent product with 5 equivalents of site-isolated MCPBA for 14 hours gave trans-stilbene oxide in 83% yield. The $^1$H and $^{13}$C NMR spectra agreed with those reported in the literature. $^1$H NMR ($CDCl_3$): δ7.33-7.38 (m, 10H), 3.87 (s, 2H)$^{13}$C NMR ($CDCl_3$): δ62.81, 125.47, 128.29, 128.53, 137.07.

trans-2,3-Bis(4-acetoxyphenyl)oxirane. Reaction of 4-acetoxystyrene with Grubbs' second generation catalyst for 6 hours, followed by reaction of the subsequent product with 5 equivalents of site-isolated MCPBA for 9 hours gave the target epoxide, in 67% yield. The $^1$H and $^{13}$C NMR spectra agreed with those reported in the literature.[8] $^1$H NMR ($CDCl_3$): δ 2.36 (s, 3H) 3.82 (s, 1H), 7.19-7.24 (overlapping doublets, 4H)$^{13}$C NMR ($CDCl_3$): δ21.20, 62.77, 125.41, 129.21, 134.21, 138.06.

trans-2,3-Bis(4-(chloromethyl)phenyl)oxirane. Reaction of 4-vinylbenzyl chloride with Grubbs' second generation catalyst for 5 hours, followed by reaction of the subsequent product with 5 equivalents of site-isolated MCPBA for 11 h gave target epoxide in 68% isolated yield. $^1$H NMR ($CDCl_3$): δ 3.87 (s, 3H), 4.39 (s 1H), 6.95-7.22 (m, 8H)$^{13}$C NMR ($CDCl_3$): δ 62.81, 125.47, 128.29, 128.53, 137.07, 77.03, 51.44.

trans-2,3-Bis(4-methylphenyl)oxirane. Reaction of 4-methylstyrene with Grubbs' second generation catalyst for 5 hours, followed by reaction of the subsequent product with 5 equivalents of site-isolated MCPBA for 15 hours gave target epoxide in 69% isolated yield. The 1H and $^{13}$C NMR spectra agreed with those reported in the literature. $^1$H NMR ($CDCl_3$): δ2.36 (s, 3H) 3.82 (s, 1H), 7.19-7.24 (overlapping doublets, 4H) $^{13}$C NMR ($CDCl_3$): δ21.20, 62.77, 125.41, 129.21, 134.21, 138.06.

Determination of amount of ruthenium that leached from the interior of the thimble under the conditions used in FIG. 5 and reported in Table 5 in the text. In a glovebox, Grubbs' second generation catalyst (43 mg, 0.05 mmole) was placed in a PDMS thimble contained in a Schlenk flask. The flask was sealed, removed from the glove box, and placed under $N_2$. To interior of the thimble was added 1 mL of $CH_2Cl_2$/BMIM followed by diethyl diallylmalonate (300 μL, 1.25 mmoles). To the exterior of the thimble was added 4 of mL 1/1 $MeOH/H_2O$. After 4, 8, 12, and 16 hours, an aliquot (0.5 mL) of solvent on the exterior of the thimble was removed and these samples were analyzed using ICP-MS for ruthenium concentration.

Determination of amount of ruthenium that leached during the recycling reactions as shown in FIG. 8 in the text. In a glovebox, Grubbs' second generation catalyst (43 mg, 0.05 mmole) was placed in a PDMS thimble contained in a Schlenk flask. The flask was sealed, removed from the glove box, and placed under $N_2$. To the thimble was added 1 mL of $CH_2Cl_2$ followed by diethyl diallylmalonate (300 μL, 1.25 mmoles), and the reaction was left stirring for 1 hour. To the exterior of the thimble, 20 mL of MeOH was added and allowed to stir for 1 hour. All solvent on the exterior of the thimble was then removed and the concentration of ruthenium in the solvent was analyzed using ICP-MS. For cycles 2 through 4 we added an additional 20 mL of MeOH to the exterior of the thimble and allowed it to stir for 1 hour. The solvent on the exterior was removed after each cycle and analyzed for ruthenium using ICP-MS. The results are summarized below (Table 8).

TABLE 8

Summary of ICP-MS data showing that the Grubbs' catalyst remained >97% encapsulated for each recycling cycle.

| Cycle | [a][Ru] (mg/mL) | [a][G2]$_{exterior}$ (mg/mL) | $\frac{[G2]_{interior}}{[a][G2]_{exterior}}$ | [b]Total Ru in exterior (%) |
|---|---|---|---|---|
| 1 | 0.007 | 0.060 | 720 | 2.8 |
| 2 | 0.007 | 0.056 | 760 | 2.6 |
| 3 | 0.006 | 0.054 | 770 | 2.6 |
| 4 | 0.004 | 0.034 | 1170 | 1.7 |

[a]These calculations assume that the Ru on the exterior was the Grubbs' catalyst. This assumption is unlikely, but it is used to illustrate the upper limit for how much of the Grubbs' catalyst (as opposed to Ru) leached from the interior of the thimbles.
[b]Amount of Ru that leached from the interior to the exterior of the thimble

EXAMPLE 3

To investigate the general applicability of the site-isolation methods of the invention to the following reaction,

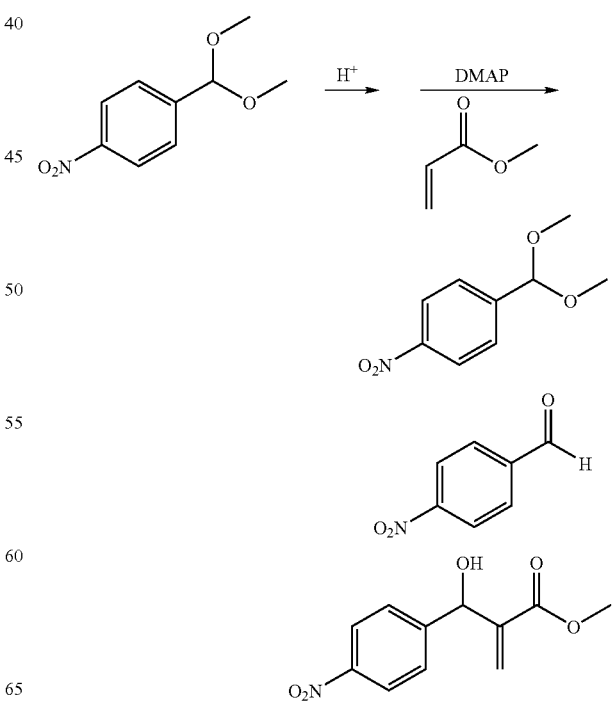

several catalysts were studied including PTSA, DMAP, $PB_{DMAP}$, $PB_{PTSA}$, and $LP_{DMAP}$. Commercially available polymer beads with either DMAP or PTSA bonded to their interiors and exteriors were used to mimic the use of star polymers in this study. First, a series of control experiments were completed where all of the reagents and catalysts were added to a glass vial without the presence of a PDMS thimble (entries 7-12 in Table 9). In reactions with free PTSA or DMAP, the conversions to product were all very low due to the catalysts quenching one another. Reactions with $PB_{PTSA}$ and $LP_{DMAP}$ had a 15% conversion to product which indicated that some of the DMAP and PTSA did not quench each other, and the reaction with $PB_{PTSA}$ and $PB_{DMAP}$ as catalysts had a 50% conversion to product. The last result was not surprising because the polymer beads are large (300 mesh for $PB_{DMAP}$ and 45 mesh for $PB_{PTSA}$) and sterically protect the catalysts from quenching each other.

In a second set of experiments, PDMS thimbles were used to site-isolate the acid catalysts from the basic catalysts. In each of these experiments, PTSA or $PB_{PTSA}$ were added to the interior of the thimbles with the solvent. DMAP, $LP_{DMAP}$, or $PB_{DMAP}$ were added to the exterior of the thimbles in the same solvent mixture and with four equivalents of methyl acrylate. The acetal was added to the interior and then the glass flask was closed and the contents were heated to 70° C. for 96 hours.

The results in entries 1-6 in Table 9 show that the PDMS thimbles were successful in site-isolating the catalyst in these reactions. The best results were obtained with $LP_{DMAP}$ and either PTSA or $PB_{PTSA}$ where the conversions reached 93%. In comparison, reactions without PDMS thimbles reached conversions of only 4 and 15%, respectively. This result is exciting because it demonstrates that free PTSA could be site-isolated from catalysts bonded to linear polymers. This result is not possible without PDMS thimbles because PTSA is free to diffuse and quench DMAP bonded along the polymer. A major challenge in the field of polymer bound catalysis is to keep small molecules that poison polymer-bound catalysts from the catalysts while still allowing the catalysts to react with small molecules in solution. These requirements appear to be at odds with one another because of the difficulties of site-isolating small molecules while allowing others to react, but success can be had by using PDMS thimbles as site-isolation vehicles.

The reactions with PTSA or $PB_{PTSA}$ and $PB_{DMAP}$ reached slightly lower conversions than those with $LP_{DMAP}$. This difference may be attributed to the lower reactivity of catalysts within the polymer beads due to either the slowed diffusion of the reactants within the polymer or that the beads swell but are not soluble in the solvent. Still, these results demonstrate that the polymer beads can be site-isolated from each other and that free PTSA can be site-isolated from polymer beads containing DMAP.

The lowest conversions with PDMS thimbles were observed in reactions catalyzed by PTSA or $PB_{PTSA}$ and DMAP. These results were not surprising because DMAP had a faster flux through PDMS than the aldehyde, so it would be expected that the DMAP would be slowly quenched by flux to the interior of the thimbles. It is notable that even with these limitations, the reaction with PTSA and DMAP reached 71% conversion with PDMS thimbles and 0% conversion without them. These results indicate that only minor changes to the structure of a catalyst to affect its flux may be necessary for site-isolation and higher success in reactions with PDMS thimbles.

Recycling of $LP_{DMAP}$ was attempted with entry 4 from Table 9. The polymer was isolated by precipitation into petroleum ether multiple times (see experimental section). The $^1H$ NMR spectrum showed that the polymer was protonated. It was therefore deprotonated by reaction with KOH at 50° C. for 12 hours. The deprotonated polymer was recovered in 47% yield and verified by $^1H$ NMR spectroscopy.

Experimental

Fabrication of PDMS thimbles: Fisherbrand screw thread glass vials (19 mm×65 mm) were added to a dessicator with 3 drops of trichloro(1H,1H,2H,2H-perfluorooctyl)silane and placed under a static vacuum for 12 hours to silanize the glass to allow for easy removal of the thimbles after fabrication. Commercially available PDMS (Sylgard 184) was mixed as two components in a 10:1 ratio (by mass) and degassed for approximately 2 hours. The glass vials were dipped into the PDMS mixture and turned upside down and placed in a 65° C. oven overnight to cross-link. Following the curing process, the top of the vials were cut around the cap with a razor blade and placed in hexanes to delaminate the thimbles from the vials for 2 hours. The hexanes were decanted and the thimbles were soaked twice in $CH_2Cl_2$ for 2 hours each time. The thimbles were dried overnight in a 125° C. oven and ready for use. The average size of PDMS thimbles were 5 cm tall by 2 cm wide with 100 micron thick walls.

Cascade reactions without PDMS thimbles: In a glass scintillation vial (20 mL) was added $PB_{PTSA}$ (0.283 g, 0.7065 mmol of PTSA) and 1-(dimethoxymethyl)-4-nitrobenzene (0.557 g, 2.826 mmol) dissolved in DMF (5.6 mL)/$H_2O$ (0.8 mL). $LP_{DMAP}$ (0.235 g, 0.7065 mmol of DMAP) was added to the reaction mixture followed by methyl acrylate (0.509 mL, 5.652 mmol). The vial was sealed tightly and placed in a 70° C. oil bath for 96 hours. The vial was removed from the oil bath and allowed to cool for 0.5 hours. The solvent was removed in vacuo and a $^1H$ NMR spectrograph was recorded in $CDCl_3$ to determine 15% conversion to product.

Cascade reactions with PDMS thimbles: In a glass scintillation vial (20 mL) was placed a PDMS thimble. Then $PB_{PTSA}$ (0.283 g, 0.7065 mmol of PTSA) and 1-(dimethoxymethyl)-4-nitrobenzene (0.557 g, 2.826 mmol) dissolved in DMF (2.8 mL)/$H_2O$ (0.4 mL) was added to the interior of the thimble. $LP_{DMAP}$ (0.235 g, 0.7065 mmol of DMAP) was dissolved in DMF (2.8 mL) and added to the exterior of the PDMS thimble followed by $H_2O$ (0.2 mL) and methyl acrylate (1.02 mL, 11.304 mmol). The vial was capped tightly and placed in a 70° C. oil bath for 96 hours. The vial was removed from the oil bath and allowed to cool for 0.5 hours. The interior contents and exterior contents were removed from the vial and combined. The solvent was filtered to remove the polymer bound catalyst followed by removal of the solvent in vacuo. The conversion was found by $^1H$ NMR spectroscopy. The residue was dissolved in MeOH (1 mL)$CH_2Cl_2$ (9 mL) and subsequently precipitated into petroleum ether (50 mL). The solvent was decanted and saved and the procedure was repeated 3 times. The combined ethereal solvent was removed in vacuo and the Baylis-Hillman adduct (0.421 g, 63% yield) was isolated as a viscous yellow oil by column chromatography using Hexanes/EtOAc (70/30). $^1H$ NMR (300 MHz, $CDCl_3$, δ): 8.21 (d, J=8.7 Hz, 2H, Ar H), 7.58 (d, J=8.1 Hz, 2H, Ar H), 6.40 (s, 1H, C=$CH_2$), 5.86 (s, 1H, C=$CH_2$), 5.63 (d, J=6.3 Hz, CHOH), 3.75 (s, 3H, $OCH_3$), 3.24 (d, J=6.3 Hz, CHOH). $^{13}C$ NMR (75.48 MHz; $CDCl_3$, δ): 166.0, 148.7, 147.0, 141.0, 127.2, 126.6, 123.2, 71.7, 51.8.

TABLE 9

Results for cascade sequences (entries 1-6) and control reactions (entries 7-12).

| Entry[a] | Acid Catalyst[b] | DMAP Catalyst[c] | PDMS Thimble | Product (%)[d] | Aldehyde (%)[d] | Acetal (%)[d] | Yield (%)[e] |
|---|---|---|---|---|---|---|---|
| 1 | PTSA•H$_2$O | LP$_{DMAP}$ | Yes | 93 | 5 | 2 | 65 |
| 2 | PTSA•H$_2$O | PB$_{DMAP}$ | Yes | 80 | 16 | 4 | 62 |
| 3 | PTSA•H$_2$O | DMAP | Yes | 71 | 24 | 5 | 50 |
| 4 | PB$_{PTSA}$ | LP$_{DMAP}$ | Yes | 93 | 4 | 3 | 63 |
| 5 | PB$_{PTSA}$ | PB$_{DMAP}$ | Yes | 83 | 12 | 5 | 67 |
| 6 | PB$_{PTSA}$ | DMAP | Yes | 71 | 22 | 7 | 48 |
| 7 | PTSA•H$_2$O | LP$_{DMAP}$ | No | 4 | 51 | 45 | — |
| 8 | PTSA•H$_2$O | PB$_{DMAP}$ | No | 3 | 41 | 56 | — |
| 9 | PTSA•H$_2$O | DMAP | No | 0 | 16 | 84 | — |
| 10 | PB$_{PTSA}$ | LP$_{DMAP}$ | No | 15 | 65 | 20 | — |
| 11 | PB$_{PTSA}$ | PB$_{DMAP}$ | No | 50 | 38 | 12 | — |
| 12 | PB$_{PTSA}$ | DMAP | No | 8 | 48 | 44 | — |

[a]Reaction time in each case was 96 h.
[b]25 mole % catalyst used, PB$_{PTSA}$ = commercially available polymer bound p-toluenesulfonic acid (2.5 mmol/g), PTSA•H$_2$O = p-toluenesulfonic acid monohydrate.
[c]25 mole % catalyst used, PB$_{DMAP}$ = commercially available polymer bound dimethylaminopyridine (3.0 mmol/g), LP$_{DMAP}$ = linear polymer containing 51% styrene/49% dimethylaminopyridine. DMAP = 4-(dimethylamino)pyridine.
[d]Conversions determined by $^1$H NMR spectroscopy.
[e]Isolated yield achieved by column chromatography with 70% hexanes/30% ethyl acetate.

EXAMPLE 4

A method for the site isolation of a homogeneous Pd catalysts that does not require modification of their ligand structures or is adversely affected by the homogeneous/colloid fluxional nature of the catalyst is described below. Commercially available Pd catalysts were used and site-isolated by encapsulation within hollow macroscopic thimbles composed of polydimethylsiloxane (PDMS). The thimbles had widths of 2 cm, heights of 5 cm, and walls that were 100-200 microns thick; dozens of these thimbles could be fabricated in a day. The catalysts were based on "ligandless" PdCl$_2$ that are highly polar and soluble only in protic solvents. The catalysts were added to the interiors of the thimbles and did not flux to the exterior, but organic molecules had high flux to the exterior. The reason for the difference in flux was the hydrophobic nature of PDMS; PdCl$_2$ was simply not soluble in this polymer due to its highly polar structure, but organic molecules were soluble. This simple difference in solubility required Pd catalysts to remain encapsulated while organic molecules were free to flux through the walls of the thimble. The Pd catalyst were recycled at levels up to >99.998%, and the products possessed molecules had high flux through the walls.

Results and Discussion

Several examples of the Wacker-Tsuji oxidation of olefins and homocoupling of arylboronic acids were completed on the interior of PDMS thimbles (Table 10). Standard conditions were used with a variety of different solvents to demonstrate that the thimbles were compatible with each of them. Each reaction went to quantitative conversions with lower yields found for the Wacker-Tsuji oxidations than the coupling reactions. These low yields are common for this reaction due to by-product formation, and represent limitations of the reaction rather than problems with the thimbles. This method did not place any limitations on the catalysts or reagents. For instance, the homocoupling reactions required the addition of p-toluenesulfonyl chloride, and the addition of this reagent was readily accommodated by this method. No concern for the reactive state (homogeneous versus colloidal) of the Pd catalyst was necessary because the reaction was run under standard conditions.

TABLE 10

Wacker-Tsuji Oxidations and Homocoupling Reactions with PdCl$_2$ Catalysts

Wacker-Tsuji Oxidation:
R—CH=CH$_2$ → (PdCl$_2$/CuCl/O$_2$, Solvent) → R—C(O)—CH$_3$ Pd-Mediated Homocoupling:
R′—C$_6$H$_4$—B(OH)$_2$ → (PdCl$_2$/Na$_2$CO$_3$, p-TsCl/Solvent) → (R′—C$_6$H$_4$—)$_2$

| Substrate | Reaction Solvent | Extracting Solvent | Product | Product Number | [a]Yield (%) |
|---|---|---|---|---|---|
| styrene | MeOH/H$_2$O | Hexanes | acetophenone | 1 | [b]73 |

TABLE 10-continued

Wacker-Tsuji Oxidations and Homocoupling Reactions with PdCl₂ Catalysts

Wacker-Tsuji Oxidation $$R\text{−CH=CH}_2 \xrightarrow{\text{PdCl}_2/\text{CuCl}/\text{O}_2}_{\text{Solvent}} R\text{−C(=O)−CH}_3$$

Pd-Mediated Homocoupling $$R'\text{−C}_6\text{H}_4\text{−B(OH)}_2 \xrightarrow{\text{PdCl}_2/\text{Na}_2\text{CO}_3}_{\text{p-TsCl/Solvent}} R'\text{−(C}_6\text{H}_4\text{)}_2$$

| Substrate | Reaction Solvent | Extracting Solvent | Product | Product Number | $^a$Yield (%) |
|---|---|---|---|---|---|
| CH₂=CH−CH(Me)−(CH₂)₃−C(Me)₂−OBn | DMF/H₂O | Hexanes | CH₃−C(=O)−CH(Me)−(CH₂)₃−C(Me)₂−OBn | 2 | $^c$56 |
| C₆H₅−B(OH)₂ | H₂O | CH₂Cl₂ | (C₆H₅)₂ | 3 | $^d$93 |
| 4-OHC−C₆H₄−B(OH)₂ | EtOH/H₂O | CH₂Cl₂ | (4-OHC−C₆H₄)₂ | 4 | $^d$89 |
| 4-Br−C₆H₄−B(OH)₂ | EtOH/H₂O | CH₂Cl₂ | (4-Br−C₆H₄)₂ | 5 | $^d$93 |

$^a$Isolated yield determined after column chromatography.
$^b$0.05 equivalents PdCl₂ used.
$^c$0.1 equivalents PdCl₂ used.
$^d$0.03 equivalents PdCl₂ used.

To isolate the products on the exterior of the thimbles while keeping the Pd on the interior, 25 mL of solvent was added to the exterior of the thimble after each reaction was complete. The product partitioned to the exterior and was readily isolated, but the Pd catalysts remained on the interior. To ensure complete isolation, the product was extracted from the interior with two to three batches of solvent on the exterior of the thimbles.

The methods of the invention allowed the Pd catalysts to be recycled and to be site-isolated from the reaction products. In separate experiments, the Wacker-Tsuji oxidation of styrene and the homocoupling of phenylboronic acid were carried out on the interior of PDMS thimbles. The product was extracted from the thimbles by the addition of 25 mL of solvent on the exterior and the amount of Pd on the exterior was measured by inductively coupled plasma-mass spectrometry (ICP-MS; Table 11). ICP-MS measured the concentration of Pd, but the catalyst used in these reactions was PdCl₂. The values shown in Table 11 reflect the concentrations of Pd (not PdCl₂) due to the instrument used to find its concentrations and the fluxional nature of the Pd catalysts that result in multiple Pd species present at the same time. To find the ratio of Pd/product, the isolated yields from Table 10 for these reactions were used to find the amount of product on the exterior of the thimbles.

In two sets of control experiments, these reactions were completed under identical conditions but in glass vials in the absence of PDMS thimbles. In the first set of control experiments, the products were isolated by liquid-liquid extractions after the addition of 50 mL of water to fully dissolve the Pd catalyst followed by three extractions with organic solvents as listed in Table 11. In a second set of control experiments, the reactions were completed in glass vessels with the solvents indicated in Table 11, and the products were extracted without the addition of excess water. In both sets of experiments, a variety of solvents were tested to complete the reaction and extract the product.

TABLE 11

ICP-MS Data to Demonstrate Site-Isolation of Pd

| Entry | $^a$Method | Reaction Solvent | Extracting Solvent | $^b$Exterior ppm (Pd/Product) | Pd Site-Isolated (%) |
|---|---|---|---|---|---|
| 1a | PDMS | DMF/H₂O | Hexanes | <2.1 | >99.998 |
| 1b | L-L | DMF/H₂O | Hexanes | 49.2 | 99.959 |
| 1c | Extract | DMF/H₂O | Hexanes | 21.0 | 99.983 |
| 2a | PDMS | MeOH/H₂O | CH₂Cl₂ | <2.2 | >99.998 |
| 2b | L-L | MeOH/H₂O | CH₂Cl₂ | 32.3 | 99.973 |
| 2c | Extract | MeOH/H₂O | CH₂Cl₂ | 416.8 | 99.655 |
| 3a | PDMS | MeOH/H₂O | Hexanes | 16.1 | 99.985 |
| 3b | L-L | MeOH/H₂O | Hexanes | 28.2 | 99.977 |
| 3c | Extract | MeOH/H₂O | Hexanes | 32.1 | 99.973 |
| 4a | PDMS | DMF/H₂O | CH₂Cl₂ | 277.7 | 99.775 |

TABLE 11-continued

ICP-MS Data to Demonstrate Site-Isolation of Pd

| Entry | [a]Method | Reaction Solvent | Extracting Solvent | [b]Exterior ppm (Pd/Product) | Pd Site-Isolated (%) |
|---|---|---|---|---|---|
| 4b | L-L | DMF/$H_2O$ | $CH_2Cl_2$ | 1173 | 99.026 |
| 4c | Extract | DMF/$H_2O$ | $CH_2Cl_2$ | 9099 | 92.980 |
| 5a | [c]PDMS | $H_2O$ | $CH_2Cl_2$ | 13.8 | 99.968 |
| 5b | [c]L-L | $H_2O$ | $CH_2Cl_2$ | 1685 | 96.216 |
| 5c | [c]Extract | $H_2O$ | $CH_2Cl_2$ | 1073 | 97.592 |
| 6 | PDMS | DMF/$H_2O$ | DMF/$H_2O$ | 12.5 | 99.988 |

[a]Three different extractions methods were indicated and performed by either the addition of solvent to the exterior of the thimble (PDMS), by liquid-liquid extractions from reactions completed in glass vials with added water (L-L), or by extracting directly from the reaction mixture following reactions in glass vials with no additional water (Extract).
[b]Based on isolated yields of corresponding product from Table 1.
[c]These entries were measured after the Pd-mediated homocoupling of phenylboronic acid, all other entries are measured after the Wacker-Tsuji oxidation of styrene.

It is clear that extractions with thimbles were more successful at site-isolating the Pd catalysts than those without thimbles. In fact, for homocoupling reactions approximately two orders of magnitude more Pd was found in the product with liquid-liquid extractions rather than with extractions using PDMS thimbles (entries 5a, b, c). In two examples (entries 1a and 2a), the amount of Pd was below detection limits for the extraction experiments with PDMS thimbles, but they were over a magnitude higher for traditional liquid-liquid extractions. In experiments with PDMS thimbles, up to >99.998% of the Pd was site-isolated on the interior and, even in the worst example of site-isolation, 99.775% of the Pd remained on the interior of the thimbles.

To demonstrate that the Pd catalysts did not flux through the thimbles due to the presence of PDMS rather than the difference in solvents used on the interior and exterior of the thimbles, an experiment with DMF/$H_2O$ (7:1 v/v) on the interior and exterior of the thimbles (entry 6 in Table 11) was completed. If the catalyst had a high flux through the PDMS walls, the concentration of Pd would be the same on the interior and exterior of the thimble. Instead, only 0.012% of the Pd originally added to the interior of the thimble diffused to the exterior in 24 hours. This result demonstrated that the thimble walls were responsible for the site-isolation.

The reason for the success of these experiments is that the Pd catalysts have low flux through the walls of the thimble but the organic products have high flux. The flux of both $PdCl_2$ and acetophenone ($C_6H_5COCH_3$) were measured by their addition to the interior of a thimble containing DMF/water and the addition of hexane to the exterior. The flux of acetophenone (0.158 mmol $cm^{-2}$ $h^{-1}$) was nearly seven orders of magnitude larger than the flux of all forms of Pd ($2.38 \times 10^{-8}$ mmol $cm^{-2}$ $h^{-1}$) as measured by ICP-MS. Flux depends on how well a molecule partitions into a membrane and its rate of diffusion while in a membrane through a set of complex equations that vary based on the geometry of the thimbles. Highly polar molecules have been shown to have low solubilities in PDMS; for instance, ionic liquids do not partition into PDMS and water does not appreciably swell it. In contrast, organic molecules partition well into PDMS and have high flux. The Pd catalysts used in these experiments are soluble in polar, protic solvents but not in apolar solvents such as toluene or PDMS. Optical micrograph of a thimble following a reaction clearly showed that the thimble was mostly clear and that the Pd catalysts did not partition into the matrix of the PDMS. In addition, the amount of Pd dissolved in the solvent on the interior was measured by ICP-MS to be 100% of the Pd that was originally added to the reaction mixture. Clearly, the Pd remained on the interior of the thimble and did not appreciable partition into PDMS.

Efforts to extend this work to other Pd catalysts were not successful. When phosphines were added to the reaction mixture, the solubility of the catalysts greatly increased in organic solvents such that they were also soluble in PDMS. In experiments with Pd catalysts and phosphines on the interior of thimbles, the catalysts were seen to flux to the exterior by eye—the solvent on the exterior became colored. This result is not surprising considering the solubility of these catalysts in apolar solvents such as toluene.

Because the Pd catalyst remained encapsulated on the interior of the thimbles, it was readily recycled (Table 12). In these experiments, $PdCl_2$ and CuCl were added to the interior of a thimble with DMF/$H_2O$ (7:1 v/v) and styrene. The oxidation to acetophenone was allowed to proceed for 24 hours, and then the product was extracted from the thimble by the addition of 25 mL of hexanes to the exterior. The hexanes were removed from the reaction vessel, the product was characterized, and additional styrene was added to the interior of the thimble. The average conversion was 94% for five cycles and the selectivity for acetophenone was 88%. These conversions and selectivities are similar to those observed by us and others in single experiments with glass vials and do not reflect limitations with the PDMS thimbles.

TABLE 12

Recycling of $PdCl_2$ for Wacker-Tsuji Oxidation of Styrene

| Cycle | [a]Conversion (%) | Ketone (%) | Acid (%) | Aldehyde (%) |
|---|---|---|---|---|
| 1 | 96 | 88 | 9 | 3 |
| 2 | 94 | 88 | 11 | 1 |
| 3 | 93 | 88 | 12 | 0 |
| 4 | 93 | 89 | 11 | 0 |
| 5 | 96 | 89 | 11 | 0 |
| 6 | 73 | 95 | 5 | 0 |

[a]Conversion for each cycle determined by $^1$H NMR spectroscopy.

Because the Pd catalyst and solvent remained site-isolated on the interior of the thimbles, they allowed for otherwise incompatible reactions to be completed on the exterior of the thimbles. For instance, the Wacker-Tsuji oxidation of p-methylstyrene was completed and the product was extracted to the exterior with hexane. Phenylmagnesium bromide was added to the exterior to react with the ketone despite the presence of water/DMF on the interior of the thimble that would, if allowed to flux through the PDMS walls, quench the entire Grignard reagent. Because of the differential flux of the ketone versus water and DMF, the reaction was successful and an isolated yield of 62% was found for the two step sequential reaction.

Conclusions

The invention provides a method to site-isolate a Pd catalyst that focuses on the materials properties of thimbles rather than the structure of the Pd catalyst. $PdCl_2$ was site-isolated within a PDMS thimble and products of reactions with this catalyst were isolated with very low levels of Pd. Organic molecules readily flux through the walls of the thimbles but $PdCl_2$ remains encapsulated due to its lack of solubility in PDMS. Importantly, catalysts in these reactions could be recycled without any alterations to their structure or by requiring them to be heterogeneous. Commercially available $PdCl_2$ was used without concern for whether the active catalyst was colloidal or single site Pd—well established reactions were readily integrated with this approach.

Experimental Section

Fabrication of PDMS thimbles. Screw thread glass vials (19 mm×65 mm) were placed in a desiccator with 3 drops of trichloro(1H, 1H,2H,2H-perfluorooctyl)silane and placed under a static vacuum for 12 hours to allow for easy removal of the thimbles after fabrication. Commercially available PDMS was mixed as two components (elastomer and curing agent) in a 10:1 ratio (by mass) and degassed for approximately 2 hours. The glass vials were dipped into the PDMS mixture, turned upside down, and placed in a 65° C. oven for approximately 1 hour. Then the vials were redipped into the PDMS mixture for a second coat, turned upside down, and placed in a 65° C. oven overnight to cross-link. Following the curing process, the top of the vials were cut around the cap with a razor blade and placed in hexanes to delaminate the thimbles from the vials for 2 hours. The hexanes were decanted and the thimbles were soaked twice in $CH_2Cl_2$ for 2 hours each time. The thimbles were dried in a 125° C. oven. The average size of PDMS thimbles was 5 cm tall by 2 cm wide with 100-200 micron thick walls.

Wacker-Tsuji oxidation of styrene in a PDMS thimble. A PDMS thimble containing $PdCl_2$ (0.025 g, 0.141 mmol) and CuCl (0.282 g, 2.82 mmol) was placed in a 2-necked Schlenk flask with a stir bar. MeOH (1.98 mL) and $H_2O$ (0.28 mL) were added to the inside of the PDMS thimble and the flask was capped with a rubber septum. A balloon filled with $O_2$ was affixed to the septum and the reaction mixture was stirred at room temperature for 1 hour. Styrene (0.323 mL, 2.82 mmol) was added to the reaction mixture and allowed to stir under an $O_2$ atmosphere for 24 hours. The PDMS thimble was swelled with hexane (2×25 mL) for 12 hours with a stir bar on the exterior of the PDMS thimble. The hexane extracts were combined and the solvent was removed in vacuo. A $^1$H NMR spectrograph was recorded in $CDCl_3$ to determine quantitative conversion of the styrene to the following products: 89% ketone, 1% aldehyde, 8% acetal, and 2% ketal. Acetophenone (0.249 g, 73% yield) was isolated as a clear liquid by column chromatography using hexanes/EtOAc (95/5). NMR spectra matched those reported in the literature.[13] $^1$H NMR (300 MHz, $CDCl_3$, δ): 7.94 (m, 2H), 7.54 (m, 1H), 7.45 (m, 2H), 2.58 (s, 3H). $^{13}$C NMR (75.48 MHz; $CDCl_3$, δ): 197.9, 137.0, 132.9, 128.4, 128.1 and 26.4.

Wacker-Tsuji oxidation of (1,1,5-trimethyl-hept-6-enyloxymethyl)-benzene in a PDMS thimble. A PDMS thimble containing $PdCl_2$ (0.100 g, 0.564 mmol) and CuCl (0.564 g, 5.64 mmol) was placed in a 2-necked Schlenk flask with a stir bar. DMF (3.96 mL) and $H_2O$ (0.56 mL) were added to the inside of the PDMS thimble and the flask was capped with a rubber septum. A balloon filled with $O_2$ was affixed to the septum and the reaction mixture was stirred at room temperature for 1 hour. The olefin starting material, 1,1,5-trimethyl-hept-6-enyloxymethyl)benzene (1.39 g, 5.64 mmol), was added to the reaction mixture and allowed to stir under an $O_2$ atmosphere for 24 hours. The PDMS thimble was swelled with hexane (2×25 mL) for 12 hour with a stir bar on the exterior of the PDMS thimble. The hexane extracts were combined and the solvent was removed in vacuo. A $^1$H NMR spectrograph was recorded in $CDCl_3$ to determine quantitative conversion of the starting material to the ketone product. 7-Benzyloxy-3,7-dimethyl-octan-2-one (0.828 g, 56% yield) was isolated as a clear liquid by column chromatography using hexanes/EtOAc (95/5). $^1$H NMR (300 MHz, $CDCl_3$, δ): 7.24 (m, 5H), 4.39 (s, 2H), 2.51 (m, 1H), 2.11 (s, 3H), 1.66-1.34 (m, 6H), 1.23 (s, 6H), 1.07 (d, J=5.4 Hz, 3H). $^{13}$C NMR (75.48 MHz; $CDCl_3$, δ): 212.6, 139.7, 128.1, 127.2, 126.9, 74.9, 63.5, 47.0, 40.5, 33.2, 27.9, 25.5, 21.5, 16.1. HRMS calcd for $C_7H_{13}O$ 113.0966, found 113.0973. Calcd for $C_{10}H_{13}O$ 149.0966, found 149.0973.

Pd-mediated homocoupling of 4-bromophenylboronic acid. A PDMS thimble containing 4-bromophenylboronic acid (0.402 g, 2.00 mmol),p-toluenesulfonyl chloride (0.191 g, 1.00 mmol), $Na_2CO_3$ (0.424 g, 4.00 mmol) and $PdCl_2$ (0.011 g, 0.06 mmol) was placed in a 2-necked Schlenk flask with a stir bar. $H_2O$ (2.5 mL) and EtOH (2.5 mL) were added to the inside of the PDMS thimble, the flask was capped, and the reaction was stirred overnight for 12 hours under air. The PDMS thimble was swelled with $CH_2Cl_2$ (3×25 mL) for 2 hours with a stir bar added to the exterior of the PDMS thimble. The $CH_2Cl_2$ extracts were combined and the solvent was removed in vacuo. A $^1$H NMR spectrograph was recorded in $CDCl_3$ to determine quantitative conversion of the 4-bromophenylboronic acid to the 4,4'-dibromobiphenyl product. 4,4'-Dibromobiphenyl (0.291 g, 93% yield) was isolated as a white solid by column chromatography using hexanes/EtOAc (10/1). NMR spectra matched those reported in the literature. $^1$H NMR (300 MHz, $CDCl_3$, δ): 7.55 (d, J=8.6 Hz, 1H), 7.40 (d, J=8.6 Hz, 1H). $^{13}$C NMR (75.48 MHz; $CDCl_3$, δ): 138.9, 132.0, 128.5, 121.9.

ICP-MS sample preparation. Three different approaches were followed to gather ICP-MS data for Table 11. The three methods are labeled as PDMS, Liquid-Liquid (L-L), and Extract. Each of these approaches is described in detail once; the same method was followed for each sample.

Wacker-Tsuji oxidation in PDMS thimbles followed by extraction of the product with hexanes (PDMS Method). A PDMS thimble containing $PdCl_2$ (0.050 g, 0.282 mmol) and CuCl (0.282 g, 2.82 mmol) was placed in a 2-necked Schlenk flask with a stir bar. DMF (1.98 mL) and $H_2O$ (0.28 mL) were added to the inside of the PDMS thimble and the flask was capped with a rubber septum. A balloon filled with $O_2$ was affixed to the septum and the reaction mixture was stirred at room temperature for 1 hour. Styrene (0.323 mL, 2.82 mmol) was added to the reaction mixture and allowed to stir under an $O_2$ atmosphere for 24 hours. The PDMS thimble was swelled with hexanes (25 mL) for 24 hours with a stir bar added to the exterior of the PDMS thimble. The PDMS thimble was removed and the interior contents and exterior contents were subjected to ICP-MS measurements by the University of Iowa Hygiene Laboratory.

Wacker-Tsuji oxidation in glass vials followed by liquid-liquid extraction with hexanes (L-L Method). $PdCl_2$ (0.050 g, 0.282 mmol) and CuCl (0.282 g, 2.82 mmol) were placed in a glass vial with a stir bar. DMF (1.98 mL) and $H_2O$ (0.28 mL) were added to the vial, and the vial was capped with a rubber septum. A balloon filled with $O_2$ was affixed to the septum and the reaction mixture was stirred at room temperature for 1 hour. Styrene (0.323 mL, 2.82 mmol) was added to the reaction mixture and allowed to stir under an $O_2$ atmosphere for 24 hours. The reaction mixture was transferred to a separatory funnel with 50 mL $H_2O$ and extracted with hexanes (3×50 mL). The hexanes was concentrated in vacuo and subjected to ICP-MS measurements by the University of Iowa Hygiene Laboratory.

Wacker-Tsuji oxidation in glass vials followed by extraction with hexanes and no added water (Extract Method). $PdCl_2$ (0.050 g, 0.282 mmol) and CuCl (0.282 g, 2.82 mmol) were placed in a glass vial with a stir bar. DMF (1.98 mL) and $H_2O$ (0.28 mL) were added to the vial and the vial was capped with a rubber septum. A balloon filled with $O_2$ was affixed to the septum and the reaction mixture was stirred at room temperature for 1 hour. Styrene (0.323 mL, 2.82 mmol) was added to the reaction mixture and allowed to stir under an $O_2$ atmosphere for 24 hours. The reaction mixture was transferred to a separatory funnel and 25 mL hexanes was added. The hexanes layer was separated then concentrated in vacuo and subjected to ICP-MS measurements by the University of Iowa Hygiene Laboratory.

Sequential reaction of a Wacker-Tsuji oxidation followed by Grignard reduction. A PDMS thimble containing PdCl$_2$ (0.100 g, 0.564 mmol) and CuCl (0.564 g, 5.64 mmol) was placed in a 2-necked Schlenk flask with a stir bar. DMF (3.96 mL) and H$_2$O (0.56 mL) were added to the inside of the PDMS thimble and the flask was capped with a rubber septum. A balloon filled with O$_2$ was affixed to the septum and the reaction mixture was stirred at room temperature for 1 hour. p-Methylstyrene (0.742 mL, 5.64 mmol) was added to the reaction mixture and allowed to stir under an O$_2$ atmosphere for 24 hours. The PDMS thimble was swelled with hexanes (30 mL) for 0.5 hours with a stir bar added to the exterior of the PDMS thimble. Phenylmagnesium bromide (3M in Et$_2$O, 18.8 mL, 56.4 mmol) was added to the exterior of the thimble and stirred under N$_2$ for 12 h. The exterior solvent was removed and the PDMS thimble was swelled with Et$_2$O (4×50 mL). The combined solvents were transferred to a separatory funnel and 3N HCl (200 mL) was added. 3N HCl (200 mL) was used two more times to extract from the organic layer then the organic layer was dried over Na$_2$SO$_4$ and filtered. The organic solvents were concentrated in vacuo. 1-Phenyl-1-p-tolyl-ethanol (0.737 g, 62% yield) was isolated by column chromatography using hexanes/EtOAc (95/5). NMR spectra agree with those reported in the literature. $^1$H NMR (300 MHz, CDCl$_3$, δ): 7.33 (d, J=8.1 Hz, 2H), 7.17 (m, 5H), 7.03 (d, J=8.1 Hz, 2H), 2.62 (s, 1H), 2.25 (s, 3H), 1.81, (s, 3H). $^{13}$C NMR (75.48 MHz; CDCl$_3$, δ): 148.1, 145.0, 136.2, 128.6, 127.9, 126.6, 125.7, 125.6, 75.8, 30.6, 20.8.

Recycling of Pd catalysts in the Wacker-Tsuji oxidation reaction. A PDMS thimble containing PdCl$_2$ (0.050 g, 0.282 mmol) and CuCl (0.282 g, 2.82 mmol) was placed in a 2-necked Schlenk flask with a stir bar. DMF (1.98 mL) and H$_2$O (0.28 mL) were added to the interior of the PDMS thimble and the flask was capped with a rubber septum. A balloon filled with O$_2$ was affixed to the septum and the reaction mixture was stirred at room temperature for 1 hour. Styrene (0.323 mL, 2.82 mmol) was added to the reaction mixture and allowed to stir under an O$_2$ atmosphere for 24 hours. The PDMS thimble was swelled with hexanes (25 mL) for 24 hours with a stir bar added to the exterior of the PDMS thimble. The hexanes were removed. One equivalent of styrene (0.323 mL, 2.82 mmol) was added to the interior of the PDMS thimble and allowed to react for 24 hours. The procedure was repeated for 6 cycles and the hexanes from each cycle were concentrated in vacuo. Conversions and product distributions were determined by $^1$H NMR spectroscopy.

EXAMPLE 5

The site isolation of two important inorganic catalysts (the Grubbs catalyst and the Sharpless dihydroxylation catalyst) was investigated. Each of these catalysts catalyzes their respective reactions to yields that often exceed 90% and, for the OsO$_4$ catalyst, in high enantioselectivities. Unfortunately, these catalysts poison one another such that they can not be added to the same reaction vessel, and they require different solvent systems. Furthermore, the fluxional ligand structure around OsO$_4$ precludes its attachment to a solid support, which makes its site-isolation from a second catalyst even more challenging.

The first step in these cascade reactions was the metathesis reaction catalyzed by the Grubbs second generation catalyst within a PDMS thimble. PDMS thimbles were fabricated with widths of 1.2 cm, heights of 3-5 cm, and with walls that were 100 μm thick. The fabrication was simple and dozens were made in an afternoon. The metathesis reactions were allowed to proceed to completion with reaction times from 2 to 8 h. In the second step, AD-mix (α or β from Aldrich Chemical Company) was added to the exterior of the thimbles in either a 1/1 mixture of t-butanol/H$_2$O or a 1/2/3 mixture of BMIM/H$_2$O/acetone. Here, BMIM is an abbreviation for a common ionic liquid: 1-butyl-3-methylimidazolium hexafluorophosphate. Both sets of solvent are commonly used with AD-mix and allow the reaction to proceed in high yields with high enantioselectivities. Each solvent mixture formed two layers, but in neither system was the Grubbs catalyst soluble.

TABLE 13

Results of cascade reactions

| substrate | product | time$^a$ (h/h) | AD-mix | yield/ee$^b$ (%/%) |
|---|---|---|---|---|
| 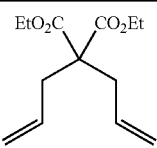 | 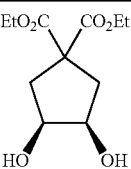 | 2/36$^c$ | α | 68$^d$ |
| Same as above | Same as above | 2/36 | α | 75$^d$ |
| 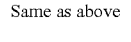 | 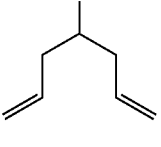 | 4/36 | α | 82/63$^e$ |
| 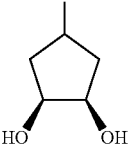 | 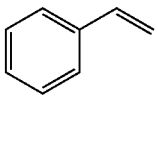 | 6/13 | α | 72/85 |

TABLE 13-continued

Results of cascade reactions

| substrate | product | time[a] (h/h) | AD-mix | yield/ee[b] (%/%) |
|---|---|---|---|---|
| styrene | 1,2-diphenyl-1,2-ethanediol (OH, OH) | 9/16 | β | 72/98 |
| 4-methylstyrene | bis(4-methylphenyl)-1,2-ethanediol | 8/12 | α | 86/84 |
| 4-methylstyrene | bis(4-methylphenyl)-1,2-ethanediol | 8/16 | β | 95/98 |
| 4-methoxystyrene | bis(4-methoxyphenyl)-1,2-ethanediol | 6/12 | α | 61/93 |
| 4-methoxystyrene | bis(4-methoxyphenyl)-1,2-ethanediol | 7/22 | β | 87/98 |
| styrene + ethyl acrylate | ethyl 2,3-dihydroxy-3-phenylpropanoate | 10/13 | β | 82/98 |
| styrene + butyl acrylate | butyl 2,3-dihydroxy-3-phenylpropanoate | 8/20 | β | 78/98 |

[a] Time for metathesis/time for dihydroxylation.
[b] Isolated yield/enantiomeric excess.
[c] 1/1 (v/v) t-BuOH/H$_2$O was used as the solvent for this reaction. 12/3 (v/v/v) BMIM/H$_2$O/acetone was used for all other reactions.
[d] The product is achiral.
[e] Diastereomeric excess.

The results in Table 13 demonstrate that this method was successful for ring closing metathesis, homocross metathesis, and heterocross metathesis reactions. The yields and enantioselectivities were high for each reaction and comparable to what was observed for AD-mix-α/β when used by others to carry out one-step reactions. This cascade sequence is very attractive for allowing simple, two step cascade reactions to be carried out on intermediates with high boiling points and varying solubilities in organic solvents. These intermediates would be challenging to remove from residual Grubbs catalyst using liquid-liquid extractions or distillation such that other methods to site-isolate the Grubbs catalyst would likely fail. In contrast, the method of the invention allows each catalyst to each react in their own solvents, at desired concentrations, and as homogenous catalysts. The catalysts were site-isolated by thin polymeric walls.

These cascade reactions required the sequential addition of catalysts to complete the reaction sequence in high yields. In many cascade sequences it is important not to add all catalysts and reagents to one reaction vessel at the same time because the order of reaction of the catalysts must be controlled. For instance, AD-mix can react with the starting materials prior to the metathesis reaction to yield a very different product than the desired one. It is necessary to control the order of reactions, and the method of the invention provides a solution to this problem by the addition of AD-mix after the metathesis reaction is complete. The sequential addition of catalysts is an advantage in some instances over a simultaneous addition and allows for inline control of the reactions to reduce waste and improve efficiency. Importantly, the method of the invention provides a solution to control the order of reaction of catalysts without requiring any synthetic transformations to them or the reagents.

It is important that this method can also be applied to reactions where the products of the first reaction in a cascade sequence have low boiling points or other physical properties that make them challenging to isolate and characterize. For instance, diallyl amine (boiling point=111-112° C.) is commonly used in metathesis reactions to demonstrate reactivities of new catalysts, but the product is rarely isolated because of its low boiling point which is estimated to be approximately 55° C. To address this problem, diallyl amine was protonated to facilitate its reaction with the Grubbs catalyst on the interior of a PDMS thimble to yield 2,5-dihydropyrrole, which was deprotonated to allow for fast flux through the walls of the thimble. $K_2Os(OH)_6$ was added to the exterior of the thimble and reacted with 2,5-dihydropyrrole to yield cis-3,4-pyrrolidinediol in 80% yield. This product had an estimated boiling point of 167° C. and was simple to isolate.

Another synthetic challenge this cascade sequence solves is how to obviate the need to isolate potentially foul smelling products. Functionalized thiophenes are important materials in medicinal chemistry, but they are often synthesized in multiple steps to lessen the need to isolate low boiling point thiols or sulfides. The synthesis of 1,1-dioxio-3,4-thiopheneoxide was undertaken to demonstrate the ability of our cascade sequence to complete a challenging set of reactions in one pot. First, diallyl sulfide was reacted with encapsulated Grubbs catalyst to yield a foul smelling intermediate with a boiling point of 90° C. This product was not isolated, rather $K_2Os(OH)_6$ was added to the exterior to dihydroxylate the olefin and oxidize the sulfur. The final product was a white solid that did not have a foul odor. This approach was an example of three reactions in one reaction vessel that eliminated the need to isolate a foul smelling intermediate.

To address how much Ru leached to the exterior of the thimble and how much Os leached to the interior, a set of control experiments with diethyl diallylmalonate were carried out and the concentrations of the metals were found using inductively coupled plasma mass spectroscopy (ICP-MS). The metathesis reaction was completed in 1 hour in 1 mL of $CH_2Cl_2$/BMIM on the interior of a PDMS thimble followed by the addition of solvent and AD-mix to the exterior of the thimble. It is clear from the results in Table 14 that the Ru was site-isolated because less than 1% diffused to exterior of the thimble even after 25 hours. This result is notable because the organic substrates in Table 13 both fluxed to the exterior and were dihydroxylated in times that were typically less than 24 hours. The flux of Os was similarly low when the 1/2/3 ($BMIM/H_2O$/acetone) solvent mixture was used for the dihydroxylation. In these reactions, the amount of Os that fluxed to the interior of the thimbles was approximately 1%. When the 1/1 (t-BuOH/$H_2O$) solvent mixture was used on the exterior of the thimbles, the amount of Os that fluxed to the interior was significantly higher. These results suggest that the Os fluxed through the walls of the thimbles rather than through vapor phase to the interior of the thimbles and that the solvent conditions can be optimized to site-isolate Os and Ru.

TABLE 14

Flux of Os and Ru through PDMS.

| solvent[a] | time[b] (h) | Os on interior (%) | Os on exterior (%) | Ru on interior (%) | Ru on exterior (%) |
|---|---|---|---|---|---|
| 1/2/3 | 10 | 1.1 | 98.9 | 99.78 | 0.22 |
| 1/2/3 | 25 | <dl | 100 | 99.40 | 0.60 |
| 1/1 | 10 | 10.3 | 89.7 | 99.65 | 0.35 |
| 1/1 | 24 | 79.4 | 20.6 | 99.09 | 0.91 |

[a]1/2/3 refers to the v/v/v mixture of BMIM/$H_2O$/acetone and 1/1 refers to the v/v mixture of t-BuOH/$H_2O$. 15 mL of the solvent was added to the exterior of the thimble.
[b]Time for the dihydroxylation reaction.

To demonstrate the incompatibility of the Grubbs catalyst with AD-mix, a series of reactions were completed without PDMS thimbles to separate the catalysts. In these reactions, diethyl diallylmalonate was reacted with the Grubbs catalyst followed by the addition of additional solvent and AD-mix to complete the dihydroxylation (Table 15). The question was not whether AD-mix poisoned the Grubbs catalyst, rather it was whether the Grubbs catalyst poisoned AD-mix. At 4 mol % of the Grubbs catalyst, only the metathesis product was observed with no evidence of the dihydroxylation product, and at loadings of 1 mol % the reaction had a conversion of only 60% to the diol. Only when the loading of the Grubbs catalyst was at or below 0.1 mol % of the malonate did the cascade reaction succeed and the diol was obtained. This result is important because many metathesis reactions reported in the literature use 1 mol % or higher loadings of catalyst.

These results demonstrated that the dihydroxylation reaction was poisoned by the Grubbs catalyst, but due to the complexity of AD-mix, it was not clear how the poisoning occurred. To investigate whether the Grubbs catalyst reacted with Os or ferricyanide that is found in AD-mix at a ratio of 1350 parts of ferricyanide for every part Os, the metathesis reaction was run to completion followed by the addition of 1 equivalent of Os for every olefin in the cyclized product. No ferricyanide was added to this reaction sequence. This reaction yielded 95% of the cyclized olefin and only 5% of the diol and clearly demonstrated that the Grubbs catalyst deactivated the Os catalyst at low loadings. The exact nature of the deactivated species was not studied, but it was consistent with the rapid reaction between the Grubbs catalyst and strong oxidants such as m-chloroperoxybenzoic acid.

TABLE 15

Cascade reactions with diethyl diallylmalonate in the absence of thimbles.

| G2[a,b] (equiv) | AD-mix-α[b] (equiv Os) | G2/Os/Fe | olefin[c] (%) | diol[c] (%) |
|---|---|---|---|---|
| 0.04 | 0.004 | 10/1/1350 | >98 | <2 |
| 0.01 | 0.004 | 2.5/1/1350 | 40 | 60 |
| 0.001 | 0.004 | 1/4/5400 | 5 | 95 |
| 0.01 | 1 | 1/10/0 | 95 | 5 |

[a]G2 refers to the Grubbs catalyst.
[b]Equivalents are based on ratio of metal to diethyl diallylmalonate.
[c]Ratio of cyclized product to the dihydroxylated product after 24 h.

Recycling of the Grubbs catalyst within the cascade sequence was possible because it was site-isolated within thimbles. In these reactions, diallyl diethylmalonate was added to the interior of PDMS thimbles in a 1/1 v/v mixture of $CH_2Cl_2$/BMIM and allowed to react for 1 hour. Next, 15 mL of 1/1 t-BuOH/$H_2O$ was added to the exterior of the thimble and the cyclized metathesis product was allowed to diffuse to the exterior. After 1 hour, the t-BuOH/$H_2O$ mixture was transferred to a different reaction vessel and AD-mix was added to it and a new batch of diethyl diallylmalonate was added to the interior of the PDMS thimble. This eluant was transferred to a new flask due to the finite lifetime of the Grubbs catalyst and the long reaction times required for AD-mix. The transfer of eluant was simple and rapid. This process was repeated seven times without loss of activity of the Grubbs catalyst, and the isolated yields of the product of the cascade sequence averaged 80%.

The methods described in this example offer a general solution for how to complete multistep cascade reactions for catalysts that poison one another or require reaction conditions that are incompatible. Notably, the structures of the catalysts were not modified, they were used as received so additional synthetic steps to them were not necessary. Cascade reactions were demonstrated for sequences that had challenging intermediates, and, importantly, recycling was possible within a cascade sequence.

All publications, patents, and patent documents discussed herein, including the entire contents of U.S. Provisional Patent Application Nos. 61/058,139 and 61/059221, as well as M. B. Runge et al., *Angew. Chem. Int. Ed.*, 2008, 47, 935-939, are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising:
   converting one or more chemical reactants to a first product by adding:
   a) one or more chemical reactants;
   b) a liquid solvent; and
   c) an organometallic catalyst to the interior of a reaction vessel that is permeable to the first product; and
   contacting the exterior of the reaction vessel with a liquid solution under conditions such that the first product passes out of the reaction vessel into the liquid solution.

2. The method of claim 1 wherein the organometallic catalyst is a Grubbs catalyst.

3. The method of claim 1 wherein the one or more chemical reactants are converted to the first product by deprotection, reduction, metathesis, alkylation, epoxidation, aldol reaction, oxidation, or dihydroxylation.

4. The method of claim 1 wherein the reaction vessel comprises a selectively permeable barrier that prevents the liquid solution from contacting the catalyst.

5. The method of claim 1 wherein the reaction vessel comprises a selectively permeable barrier that prevents one or more catalyst deactivating components in the liquid solution from contacting the catalyst.

6. The method of claim 1 wherein the reaction vessel is formed from polydimethylsiloxane.

7. The method of claim 1 wherein at least one of the one or more chemical reactants is an acetal or a ketal; the first product is the corresponding aldehyde or ketone; and the reaction vessel contains water and an acid catalyst.

8. The method of claim 7 wherein the reaction vessel comprises a selectively permeable barrier that prevents the liquid solution or one or more components in the liquid solution from entering the reaction vessel.

9. The method of claim 1 wherein at least one of the one or more chemical reactants is a diene the first product is the corresponding cyclic alkene; and the reaction vessel contains a metathesis catalyst.

10. The method of claim 9 wherein the reaction vessel comprises a selectively permeable barrier that prevents the liquid solution or one or more components in the liquid solution from entering the reaction vessel.

11. The method of claim 1 wherein at least one of the one or more chemical reactants is an arylboronic acid; the first product is the corresponding bisaryl homocoupling product; and the reaction vessel contains a palladium catalyst.

12. The method of claim 11 wherein the reaction vessel comprises a selectively permeable barrier that prevents the liquid solution or one or more components in the liquid solution from entering the reaction vessel.

* * * * *